US008173869B2

(12) United States Patent
Goldman et al.

(10) Patent No.: US 8,173,869 B2
(45) Date of Patent: May 8, 2012

(54) PLANTS EXPRESSING ENVIRONMENTAL STRESS TOLERANCES HAVING PETUNIA CBF GENES THEREIN

(75) Inventors: Stephen L. Goldman, Toledo, OH (US); Sairam Venkata Rudrabhatla, Middletown, PA (US); Madasamy Parani, Chennai (IN); Mark Styczynski, Somerville, MA (US); R. Michael Raab, Medford, MA (US)

(73) Assignees: The University of Toledo, Toledo, OH (US); Agrivida, Inc., Medford, MA (US)

( * ) Notice: Subject to any disclaimer, the term of this patent is extended or adjusted under 35 U.S.C. 154(b) by 603 days.

(21) Appl. No.: 12/090,908

(22) PCT Filed: Oct. 20, 2006

(86) PCT No.: PCT/US2006/041228
§ 371 (c)(1),
(2), (4) Date: Apr. 7, 2009

(87) PCT Pub. No.: WO2007/048030
PCT Pub. Date: Apr. 26, 2007

(65) Prior Publication Data
US 2009/0307793 A1 Dec. 10, 2009

Related U.S. Application Data

(60) Provisional application No. 60/729,194, filed on Oct. 21, 2005.

(51) Int. Cl.
*A01H 5/00* (2006.01)
*C12N 15/82* (2006.01)
*C12N 5/14* (2006.01)
*C12N 15/63* (2006.01)
*C12N 15/81* (2006.01)
*C07H 21/04* (2006.01)

(52) U.S. Cl. ....... 800/295; 800/278; 800/279; 435/69.1; 435/320.1; 435/468; 536/23.1

(58) Field of Classification Search .......................... None
See application file for complete search history.

(56) References Cited

U.S. PATENT DOCUMENTS

| 6,706,866 | B1 | 3/2004 | Thomashow et al. | |
| 6,833,446 | B1 | 12/2004 | Wood et al. | |
| 2004/0019927 | A1* | 1/2004 | Sherman et al. | 800/278 |

OTHER PUBLICATIONS

Zhang et al. (NCBI, Gen/Bank, Sequence Accession No. AY497899, Published Sep. 6, 2004).*
International Preliminary Report on Patentability, PCT/US06/41228, mailed Nov. 2, 2011.

Chen et al., "An AP2/EREBP-Type Transcription-Factor Gene from Rice is Cold-Inducible and Encodes a Nuclear-Localized Protein", *Theoretical and Applied Genetics*, Oct. 2003, pp. 972-979.
Choi et al., "Barley Cbf3 Gene Identification, Expression Pattern, and Map Location", *Plant Physiology*, Aug. 2002, pp. 1781-1787.
Cook et al., "A Prominent Role for the CBF Cold Response Pathway in Configuring the Low-Temperature Metabolome of *Arabidopsis*", *Proceedings of the National Academy of Science of the United States of America*, Oct. 19, 2004, pp. 15243-15248.
Dubouzet et al., "OsDREB genes in Rice, *Oryza sativa* L., Encode Transcription Activators That Function in Drought-, High-Salt- and Cold-Responsive Gene Expression", *The Plant Journal for Cell and Molecular Biology*, Feb. 2003, pp. 751-763.
Gao et al., "Regulation and Characterization of Four CBF Transcription Factors from *Brassica napus*", *Plant Molecular Biology*, Jul. 2002, pp. 459-471.
Gilmore et al., "Overexpression of the *Arabidopsis* CBF3 Transcriptional Activator Mimics Multiple Biochemical Changes Associated with Cold Acclimation", *Plant Physiology*, Dec. 2000, pp. 1854-1865.
Gilmour et al., "Low Temperature Regulation of the *Arabidopsis* CBF Family of AP2 Transcriptional Activators as an Early Step in Cold-Induced COR Gene Expression", *The Plant Journal for Cell and Molecular Biology*, Nov. 6, 1998, pp. 433-442.
Haake et al., "Transcription Factor CBF4 is a Regulator of Drought Adaptation in *Arabidopsis*", *Plant Physiology*, Oct. 2002, pp. 639-648.
Jaglo et al., "Components of the *Arabidopsis* C-Repeat/Dehydration-Responsive Element Factor Cold-Response Pathway are Conserved in *Brassica napus* and Other Plant Species", *Plant Physiology*, Nov. 2001, pp. 910-917.
Jaglo-Ottosen et al., "*Arabidopsis* CBF1 Overexpression Induces COR Genes and Enhances Freezing Tolerance", *Science*, Apr. 3, 1998, pp. 104-106.
Kasuga et al., "Improving Plant Drought, Salt, and Freezing Tolerance by Gene Transfer of a Single Stress-Inducible Transcription Factor", *Nature Biotechnology*, Mar. 17, 1999, pp. 287-291.
Liu et al., "Two Transcription Factors, DREB1 and DREB2, with an EREBP/AP2 DNA Domain Separate Two Cellular Signal Transduction Pathways in Drought- and Low-Temperature-Responsive Gene Expression, Respectively, in *Arabidopsis*", *The Plant Cell*, Aug. 1998, pp. 1391-1406.
Medina et al., "The *Arabidopsis* CBF Gene Gamily is Composed of Three Genes Encoding AP2 Domain-Containing Proteins Whose Expression Is Regulated by Low Temperature but not by Abscisic Acid or Dehydration", *Plant Physiology*, Feb. 1999, pp. 463-470.
Qin et al., "Cloning and Functional Analysis of a Novel DREB1/CBF Transcription Factor Involved in Cold-Responsive Gene Expression in *Zea mays* L.", *Plant and Cell Physiology*, Aug. 2004, pp. 1042-1052.
Sairam et al., "A Study on the Effect of Genotypes, Plant Growth Regulators and Sugars in Promoting Plant Regeneration via Organogenesis from Soybean Cotyledonary Nodal Callus", *Plant Cell, Tissue and Organ Culture*, Oct. 2003.
Sakuma et al., "DNA-Specificity of the ERF/AP2 Domain of *Arabidopsis* DREBs, Transcription Factors Involved in Dehydration- and Cold-Inducible Gene Expression", *Biochemical and Biophysical Research Communications*, Jan. 25, 2002, pp. 998-1009.
Zhang et al., "Freezing-Sensitive Tomato has a Functional CBF Cold Response Pathway, but a CBF Regulon That Differs from that of Freezing-Tolerant *Arabidopsis*", *The Plant Journal*, Sep. 2004, pp. 905-919.

* cited by examiner

*Primary Examiner* — Vinod Kumar
(74) *Attorney, Agent, or Firm* — McKee, Voorhees & Sease, P.L.C.

(57) ABSTRACT

The present invention provides a method of controlling a plant's tolerance to environmental stress and to a transgenic plant having the desired characteristics.

28 Claims, 14 Drawing Sheets

FIGURE 3

| Primer | SEQ ID NO: | Sequence |
|---|---|---|
| PetF4 | 1 | AATCCNAARAARCCNGCNG |
| PetR5 | 2 | ATCAGCRAARTTNARRCANGC |
| 3RACE1 | 3 | GGGAGGAAGAAGTTTCAAGAAACTCGACATCC |
| 3RACE2 | 4 | GGGAGGAAGAAGTTTCAAGAAACACGACATCC |
| 3RACE3 | 5 | GCCGGGAGGAAGAAGTTTAGAGAAACACGACA |
| 5RACE1 | 6 | GGATGTCGAGTTTCTTGAAACTTCTTCCTCCC |
| 5RACE2 | 7 | GGATGTCGTGTTTCTTGAAACTTCTTCCTCCC |
| 5RACE3 | 8 | TGTCGTGTTTCTCTAAACTTCTTCCTCCCGGC |
| ParF1 | 9 | CCTCAAACTGAAATAACATTCAGTACTAGTACT |
| ParF3 | 10 | CCTCTAACTGAAACAACATCCAATACAACC |
| ParF2 | 11 | TAACATTCAGTACTAGTACTATACACTTACTA |
| ParF4 | 12 | CAAAAACCTCAAACTGAACAACATTC |
| ParR1 | 13 | GGCAAACTACACGATGTTCTTGTCTCTCATC |
| ParR2 | 14 | TGGATCTTTCATTCAATACAAGGGCTTGG |
| ParR3 | 15 | CAGTCAAATGTCGTGGTTTGAAAAAACCG |
| ParR4 | 16 | CCGCGCCAAGTCAAACACAGACACTC |
| CBF1ProbeF | 17 | CAAGAAGTCACTCCGGCTTT |
| CBF1ProbeR | 18 | TTGCATTCAAAAGTGGCAAA |
| CBF2ProbeF | 19 | AATTCTGTTAGTACTTCTTTGGGATAG |
| CBF2ProbeR | 20 | TTAGCTGCTCACTTGGATCTTTC |

FIGURE 3A

| Primer | SEQ ID NO: | Sequence |
|---|---|---|
| CBF3ProbeF | 21 | TTGGTACCTAATATTTGGACGGTA |
| CBF3ProbeR | 22 | TCAAATGTCGTGGTTTGAAAAA |
| CBF4ProbeF | 23 | ATATTTGGGCGGTACGTCTG |
| CBF4ProbeR | 24 | AGATTTGTTTTGGACCACATGA |
| ActinF | 25 | GAAGCGCCTCTGAACCCAAA |
| ActinR | 26 | CCGCAGCTTCCATTCCAATC |
| PetCBF1 | 27 | AAGCAGTGGC ATCAACGCAG AGTACGCGGG GAAAAAACAA AAACCTCTAA CTGAAACAAC ATCCAATACA ACCATACTTT TTCTACTCTC AATATATCAG TGATCAAGAA ATGGATATCT TTGGAAGCTA TTATTCAGAC ACACTTCCTG CAGCATCAGC TCCTACTTTT TGGCCTTTAG ACGTGCCTGA ATATTCTTCA CCAATATCTG ATAATAGCAG CTGCAGTAAT AATAGAGCTA ATCATTCTGA TGAAGAGGTG ATGTTAGCTT CAAATAACCC GAAAAAGCGA GCCGGGAGGA AGAAGTTTAG AGAAACACGA CATCCAGTAT ACAGGGGAGT CAGGAAGAGG AATTCAGGCA AGTGGGTTTG TGAAGTGAGA GAACCCAATA AGCAATCAAG AATTTGGCTT GGAACATTCC CAACTGCTGA AATGGCGGCT AGAGCTCATG ACGTGGCGGC TATTGCATTT AGGGGTCGTT CTGCTTGTTT GAATTTTGCG GACTCTGCTT GGAAGTTGCC TACCCCTGCT TCTTCCGACC CCAAGGATAT TCAGAAGGCG GCCGCAGAGG CCGCCGAGGC TTTTAGGCCT TTGGAGTCAG AAGGGGTACA TTCAGCTGGA GAAGAATCAA AAGAAGAGAG CACCACTCCA GAAACAGCAG AGAGTATGTA CTTTATGGAT GAAGAGGCAC TTTTCTGCAT GCCTGGATTA CTTGCAAATA TGGCTGAAGG GCTAATGTTA CCTCCACCTC AATGTTCAGA AGTTGGAGAT CATTTTATGG AAGCTGATGC TGACATGCCT TTATGGAGTT ATTCTGTCTA ATTCTTCTAG TTATTACTCT TTTTAACATA ATGGAGTATA ATTTAGTACA GTTTCTTAAA TTAGGATTTA GGAGACATTA GTAGTTTTGT ACCTAATATT TGGATGGTAC AGTGTACCTT TTAGTAACGA TGCAAATAGT |

FIGURE 3B

| Primer | SEQ ID NO: | Sequence |
|---|---|---|
| | | ACTACTACTC TGTTCTGCTA GTATCAAGAA GTCACTCCGG CTTTGTGCAA ATCATTGGCC TAGACTTCTA AGACTATTTT AGCGGCAGTG GAACATAAGT GAGATAATAG TACTACTAAT TAGTATTAGT AATATTGATG AGAGACAAGA ACATCGTGTA GTTTGCCACT TTTGAATGCA ATATTTTAAG TAGAGGCATT AGGTGTAACA GCCTTCTCAA TGATAATCAC AGTTGAGTCA AAAAAAAAAA AAAAAAAA |
| PetCBF2 | 28 | CTAATACGAC TCACTATAGG GCAAGCAGTG GTATCAACGC AGAGTACGCG GGGAAAACAA AAACCTCAAA CTGAACAACA TTCAATATTA GTGAAACACT TTTTACTCTC TCAAAATGGA TATCTTTGGA AGCTATTATT CAGACATACT TCCTATAGAA TTGCCTGAAT ATTCTTCACC AATGTCTGAC AATAGCAGCT GCAGCAATTA TAGAGCTAAT CATTCAGATG ACGAAGTGAT GTTAGCTTCA AATAACCCCA AGAAGTGTGC TGGGAGGAAG AAGTTTAGAG AAACACGACA TCCAGTATAC AGGGGAGTCA GGAAGAGGAA CGGCAAGTGG GTTTGTGAAG TCAGAGAGCC CAATAAGAAA TCAAGAATTT GGCTTGGTTC ATTTCCAACT GCTGAAATGG CCGCTAGAGC TCACGATGTA GCGGCTATTG CATTAAGGGG TCGTTCTGCT TGCTTGAACT TGCTGACTC TGCTTGGAAG TTGCCTATCC CTGCTTCCTC CAACCCCAAG GATATTCAGA AGGCGGCCGC AGAGGCCGCC AAGGCTTTCA GGGAGTCGGG AGAAGAATCA AAGGAAGAGA GCAGTACTCG TGAAACGCCA GAAAAGATGT TCTTTATGGA TGAAGAGGCA CTTTTCTGCA TGCCAGAATT ACTTGCAAAT ATGGCTGAAG GACTAATGTT ACCTCCACCA TCTCAATGTT CAGATGTTGG AGAGCATTTT ATGGATGCTG ATGTTGACAT GCCTTTATGG AGTTATTCTA TCTAAATTAG TAATTCTGTT AGTACTTCTT TGGGATAGTC TATGATCTTC TCTATAAGCA AGTCAAGAT GCAAGCAGAA TGCTTCAAGT GAAGTTCCTT AAAAGTAGGA TTTAGGCGAT ATAGGACTAT TGGTAGCTTC GTACTCAATA TTTGGATGGT ACGTCTGTAC ATAGGTGAGG TAAATATGGT AAGATCTAGG TATTCTTATG TTTGCACCGG AAAGTGGTTT CGGCTAAATG CAAATCATTG |

FIGURE 3C

| Primer | SEQ ID NO: | Sequence |
|---|---|---|
| | | ACACTGCGGA CAAGAATATT ATAGCGTCAC CAATTCGTGA AGACTTGTGA ATTGGTGGCT TGGTTATTTC CAAGCCCTTG TATTGAATGA AAGATCCAAG TGAGCAGCTA ATTTGGGAGC AAAAAAAAAA AAAAAAAA |
| PetCBF3 | 29 | GAAGAAACAA AAACCTCAAA CTGAAATAAC ATTCAGTACT AGTACTATAC ACTTTTTACA CAAAATATCA GTGATCAAGA AATGGATATT TTTGCAAGAT ATTATTCGGA CCAACTTCCT ATAGCATCAG CTGCTACTTT TTGGCCTTTA GAAGTGGCTG AATATTCTTC ACCAATGTCT GATATTAGTA ATAATAGAGC TAATCTTTCA GATGAAGAAG TGATGTTAGC TTCAAATAAC CCAAAGAAGC GAGCTGGGAG GAAGAAGTTT CAAGAAACAC GACATCCAGT ATACAGGGGA GTGAGGAAGA GGAGTTCAGG CAAGTGGGTT TGTGAAGTGA GAGAGCCCAA TAAGAAATCA AGAATTTGGC TAGGCACATA TAATAACTGCT GAAATGGCAG CTAGAGCTCA TGACGTCGCA GCTATTGCAT TAAGGGGTCG TTCTGCTTGT CTGAACTTTG CTGACTCTGC TTGGAAGTTG CATATCCCGG CTTCCTCCAA AGCCAAGGAT ATTCAGAAGG CGGCCACAGA GGCTGCCTCG GCTTTCCAGG AATCAAAGGA AGAGGGCACT ACTCCTGAAA CGCCAGAAAA GATGCTCTTT ATGGATGAAG AGGCACTTTT CTACATGCCT GGATTACTTG CAAATATGGC TGAAGGACTA ATGTTACCTC TACCACCTCA ATGTTCAGAA GTTGGAGATC ATTTTATGGA AGCTGCTGCT GACATGCCTT TGTGGAGTTA TTCTTTCTAA TTGTTTTAGT CCAGTTTCTT AAATTAGGAT TTAGGAGACG TTAGTAGTTT GGTACCTAAT ATTTGGACGG TACAGTGTAT ACAATTTAGT AACGATGTTA GATAGTACTA CTACTCTGTT CTGCTAGAAT CAAGAAGTTC TTCTGGTTTA ATGCAGAACA GAGGATGTTT GTTATAGCGT AATTGGATTA TTTTGTTTAG GCAAGTGAAT AAGAAAATTT CTTCGGTTTT TTCAAACCAC GACATTTGAC AAAAAAAAAA AAAAAAAAA AAAA |
| PetCBF4 | 30 | GAAAATAAAA ACAAAAACCT CAAACTGAAA TAACATTCAG TACTAGTACT ATACACTTAC |

FIGURE 3D

| Primer | SEQ ID NO: | Sequence |
|---|---|---|
| | | TATTACTCTC AAAATATGAG TGATCAAGAA ATGGATATTT TTGGACGATA TTATTCTGAC CAACTTCCTA TAGCATCAGC TGCTACATTT TGGCCTTTAG AAGTGGCTGA ATATTCTGAT AATAGCAGCA GCAGCAGTAA TAATAGAGCT AATGTTTCAG ATGAAGAAGT GATGTTAGCT TCAAATAACC CAAAGAAGCG AGCTGGGAGG AAGAAGTTTC AAGAAACTCG ACATCCAGTA TATAGGGGAG TGAGGAAGAG GAATTCAGGG AAGTGGGTTT GTGAAGTGAG AGAGCCCAAT AAGAAATCAA GAATATGGCT TGGAACATAT TCAACTGCAG AAATGGCAGC TAGAGCTCAT GATGTTGCGG CTATTGCATT AAGGGGTCGT GCTGCTTGTC TAAACTTTGC TGACTCTGCT TGGAAGTTAC CTATCCCGGC TTCCTCCAAA GCCAAGGATA TCCAGAAGGC GGCCACAGAG GCCGCCGCCA CGGCTTTTCT GGAACCAGGA GAGCCTGAAA CTCGAAAAAA AAATATGTTG TTTATGGATG AAGAGGCACT TTTTTGCATG CCTGGATTAC TTGCAAATAT GGCTGAAGGA CTAATGTTAA CTCCACCTCA ATGTTATGGA GAACATTTTA TGGAAGCTGA TGCTGAAGTG CCTTTATGGA GTTATTAGAT CTCCATAATT AGACATTCTA TGATCTTCAT ACACAATATT TGGGCGGTAC GTCTGTACAT GAGTGAGATA GTAATCCGCC AGTCCCAAAA TGAGTGTCTG TGTTTGACTT GGCGCGGAGA TTAAGATAAC AGAGAAGACT TTTGAATCAT GTTGTTGTGT GTAATATGGG CCACTTATTT TTAAATCATG TGGTCCAAAA CAAATCTTGA AATTAAAGAG TTATAAAATA TGGAAAGAAT CACTCTTTTT AGACAAAAAA AAAAAAAAAA AAAAAAAAAA |
| Oligo-dT-18 | 31 | TTTTTTTTTT TTTTTTTT |
| PETCBF1 | 32 | MDIFGSYYSD TLPAASAPTF WPLDVPEYSS PISDNSSCSN NRANHSDEEV MLASNNPKKR AGRKKFRETR HPVYRGVRKR NSGKWVCEVR EPNKQSRIWL GTFPTAEMAA RAHDVAAIAF RGRSACLNFA DSAWKLPTPA SSDPKDIQKA AAEAAEAFRP LESEGVHSAG EESKEESTTP ETAESMYFMD EEALFCMPGL LANMAEGLML PPPQCSEVGD HFMEADADMP LWSYSV |

FIGURE 3E

| Primer | SEQ ID NO: | Sequence |
|---|---|---|
| PETCBF2 | 33 | MDIFGSYYSD ILPIELPEYS SPMSDNSSCS NYRANHSDDE VMLASNNPKK CAGRKKFRET RHPVYRGVRK RNGKWVCEVR EPNKKSRIWL GSFPTAEMAA RAHDVAAIAL RGRSACLNFA DSAWKLPIPA SSNPKDIQKA AAEAAKAFRE SGEESKEESS TRETPEKMFF MDEEALFCMP ELLANMAEGL MLPPPSQCSD VGEHFMDADV DMPLWSYSI |
| PETCBF3 | 34 | MDIFARYYSD QLPIASAATF WPLEVAEYSS PMSDISNNRA NLSDEEVMLA SNNPKKRAGR KKFQETRHPV YRGVRKRSSG KWVCEVREPN KKSRIWLGTY ITAEMAARAH DVAAIALRGR SACLNFADSA WKLHIPASSK AKDIQKAATE AASAFQESKE EGTTPETPEK MLFMDEEALF YMPGLLANMA EGLMLPLPPQ CSEVGDHFME AAADMPLWSY SF |
| PETCBF4 | 35 | MDIFGRYYSD QLPIASAATF WPLEVAEYSD NSSSSSNNRA NVSDEEVMLA SNNPKKRAGR KKFQETRHPV YRGVRKRNSG KWVCEVREPN KKSRIWLGTY STAEMAARAH DVAAIALRGR AACLNFADSA WKLPIPASSK AKDIQKAATE AAATAFLEPG EPETRKKNML FMDEEALFCM PGLLANMAEG LMLTPPQCYG EHFMEADAEV PLWSY |
| PetCBF1 Promoter | 36 | AAGCAGTGGC ATCAACGCAG AGTACGCGGG GAAAAAACAA AAACCTCTAA CTGAAACAAC ATCCAATACA ACCATACTTT TTCTACTCTC AATATATCAG TGATCAAGAA |
| PetCBF2 Promoter | 37 | CTAATACGAC TCACTATAGG GCAAGCAGTG GTATCAACGC AGAGTACGCG GGGAAAACAA AAACCTCAAA CTGAACAACA TTCAATATTA GTGAAACACT TTTTACTCTC TCAAA |
| PetCBF3 Promter | 38 | GAAGAAACAA AAACCTCAAA CTGAAATAAC ATTCAGTACT AGTACTATAC ACTTTTTACA CAAAATATCA GTGATCAAGA A |
| PetCBF4 Promoter | 39 | GAAAATAAAA ACAAAAACCT CAAACTGAAA TAACATTCAG TACTAGTACT ATACACTTAC TATTACTCTC AAAATATGAG TGATCAAGAA |

FIGURE 3F

| Primer | SEQ ID NO: | Sequence |
|---|---|---|
| PetCBF1 ORF | 40 | ATGGATATCT TTGGAAGCTA TTATTCAGAC ACACTTCCTG CAGCATCAGC TCCTACTTTT TGGCCTTTAG ACGTGCCTGA ATATTCTTCA CCAATATCTG ATAATAGCAG CTGCAGTAAT AATAGAGCTA ATCATTCTGA TGAAGAGGTG ATGTTAGCTT CAAATAACCC GAAAAAGCGA GCCGGGAGGA AGAAGTTTAG AGAAACACGA CATCCAGTAT ACAGGGGAGT CAGGAAGAGG AATTCAGGCA AGTGGGTTTG TGAAGTGAGA GAACCCAATA AGCAATCAAG AATTTGGCTT GGAACATTCC CAACTGCTGA ATGGCGGCT AGAGCTCATG ACGTGGCGGC TATTGCATTT AGGGGTCGTT CTGCTTGTTT GAATTTTGCG GACTCTGCTT GGAAGTTGCC TACCCCTGCT TCTTCCGACC CCAAGGATAT TCAGAAGGCG GCCGCAGAGG CCGCCGAGGC TTTTAGGCCT TTGGAGTCAG AAGGGGTACA TTCAGCTGGA GAAGAATCAA AAGAAGAGAG CACCACTCCA GAAACAGCAG AGAGTATGTA CTTTATGGAT GAAGAGGCAC TTTTCTGCAT GCCTGGATTA CTTGCAAATA TGGCTGAAGG GCTAATGTTA CCTCCACCTC AATGTTCAGA AGTTGGAGAT CATTTTATGG AAGCTGATGC TGACATGCCT TTATGGAGTT ATTCTGTCTA A |
| PetCBF2 ORF | 41 | ATGGATATCT TTGGAAGCTA TTATTCAGAC ATACTTCCTA TAGAATTGCC TGAATATTCT TCACCAATGT CTGACAATAG CAGCTGCAGC AATTATAGAG CTAATCATTC AGATGACGAA GTGATGTTAG CTTCAAATAA CCCCAAGAAG TGTGCTGGGA GGAAGAAGTT TAGAGAAACA CGACATCCAG TATACAGGGG AGTCAGGAAG AGGAACGGCA AGTGGGTTTG TGAAGTCAGA GAGCCCAATA AGAAATCAAG AATTTGGCTT GGTTCATTTC CAACTGCTGA ATGGCCGCT AGAGCTCACG ATGTAGCGGC TATTGCATTA AGGGGTCGTT CTGCTTGCTT GAACTTTGCT GACTCTGCTT GGAAGTTGCC TATCCCTGCT TCCTCCAACC CCAAGGATAT TCAGAAGGCG GCCGCAGAGG CCGCCAAGGC TTTCAGGGAG TCGGGAGAAG AATCAAAGGA AGAGAGCAGT ACTCGTGAAA CGCCAGAAAA GATGTTCTTT ATGGATGAAG AGGCACTTTT CTGCATGCCA |

FIGURE 3G

| Primer | SEQ ID NO: | Sequence |
|---|---|---|
| | | GAATTACTTG CAAATATGGC TGAAGGACTA ATGTTACCTC CACCATCTCA ATGTTCAGAT GTTGGAGAGC ATTTTATGGA TGCTGATGTT GACATGCCTT TATGGAGTTA TTCTATCTAA |
| PetCBF3 ORF | 42 | ATGGATATTT TTGCAAGATA TTATTCGGAC CAACTTCCTA TAGCATCAGC TGCTACTTTT TGGCCTTTAG AAGTGGCTGA ATATTCTTCA CCAATGTCTG ATATTAGTAA TAATAGAGCT AATCTTTCAG ATGAAGAAGT GATGTTAGCT TCAAATAACC CAAAGAAGCG AGCTGGGAGG AAGAAGTTTC AAGAAACACG ACATCCAGTA TACAGGGGAG TGAGGAAGAG GAGTTCAGGC AAGTGGGTTT GTGAAGTGAG AGAGCCCAAT AAGAAATCAA GAATTTGGCT AGGCACATAT ATAACTGCTG AAATGGCAGC TAGAGCTCAT GACGTCGCAG CTATTGCATT AAGGGGTCGT TCTGCTTGTC TGAACTTTGC TGACTCTGCT TGGAAGTTGC ATATCCCGGC TTCCTCCAAA GCCAAGGATA TTCAGAAGGC GGCCACAGAG GCTGCCTCGG CTTTCCAGGA ATCAAAGGAA GAGGGCACTA CTCCTGAAAC GCCAGAAAAG ATGCTCTTTA TGGATGAAGA GGCACTTTTC TACATGCCTG GATTACTTGC AAATATGGCT GAAGGACTAA TGTTACCTCT ACCACCTCAA TGTTCAGAAG TTGGAGATCA TTTTATGGAA GCTGCTGCTG ACATGCCTTT GTGGAGTTAT TCTTTCTAA |
| PetCBF4 ORF | 43 | ATGGATATTT TTGGACGATA TTATTCTGAC CAACTTCCTA TAGCATCAGC TGCTACATTT TGGCCTTTAG AAGTGGCTGA ATATTCTGAT AATAGCAGCA GCAGCAGTAA TAATAGAGCT AATGTTTCAG ATGAAGAAGT GATGTTAGCT TCAAATAACC CAAAGAAGCG AGCTGGGAGG AAGAAGTTTC AAGAAACTCG ACATCCAGTA TATAGGGGAG TGAGGAAGAG GAATTCAGGG AAGTGGGTTT GTGAAGTGAG AGAGCCCAAT AAGAAATCAA GAATATGGCT TGGAACATAT TCAACTGCAG AAATGGCAGC TAGAGCTCAT GATGTTGCGG CTATTGCATT AAGGGGTCGT GCTGCTTGTC TAAACTTTGC TGACTCTGCT TGGAAGTTAC CTATCCCGGC TTCCTCCAAA GCCAAGGATA TCCAGAAGGC GGCCACAGAG |

FIGURE 3H

| Primer | SEQ ID NO: | Sequence |
|---|---|---|
| | | GCCGCCGCCA CGGCTTTTCT GGAACCAGGA GAGCCTGAAA CTCGAAAAAA AAATATGTTG TTTATGGATG AAGAGGCACT TTTTTGCATG CCTGGATTAC TTGCAAATAT GGCTGAAGGA CTAATGTTAA CTCCACCTCA ATGTTATGGA GAACATTTTA TGGAAGCTGA TGCTGAAGTG CCTTTATGGA GTTATTAG |
| PEtCBF1 AP2 | 44 | PVYRGVRKRN SGKWVCEVRE PNKQSRIWLG TFPTAEMAAR AHDVAAIAFR GRSACLNFAD S |
| PECBF2 AP2 | 45 | PVYRGVRKRN GKWVCEVREP NKKSRIWLGS FPTAEMAAVA HDVAAIKLRG PDALTNFADS |
| PETCBF1.1 | 46 | MDIFGSYYSD TLPAASAPTF WPLDVPEYSS PISDNSSCSN NRAHHSDEEV MLASNNPKKR AGRKKFRETR HPVYRGVRKR NSGKWVCEVR EPNKQSRIWL GTFPTAEMAA VAHDVAAIKF RGVEADINFA DSAWKLPTPA SSDPKDIQKA AAEAAEAFRP LESEGVHSAG EESKEESTTP ETAESMYFMD EEALFCMPGL LANMAEGLML PPPQCSEVGD HFMEADADMP LWSYSV |
| PETCBF1.2 | 47 | MDIFGSYYSD TLPAASAPTF WPLDVPEYSS PISDNSSCSN NRAHHSDEEV MLASNNPKKR AGRKKFRETR HPVYRGVRKR NSGKWVCEVR EPNKQSRIWL GTFPTAEMAA VAHDVAAIKF RGTNAVTNFA DSAWKLPTPA SSDPKDIQKA AAEAAEAFRP LESEGVHSAG EESKEESTTP ETAESMYFMD EEALFCMPGL LANMAEGLML PPPQCSEVGD HFMEADADMP LWSYSV |
| PETCBF1.3 | 48 | MDIFGSYYSD TLPAASAPTF WPLDVPEYSS PISDNSSCSN NRAHHSDEEV MLASNNPKKR AGRKKFRETR HPVYRGVRKR NSGKWVCEVR EPNRQSRIWL GTFPTAEMAA KAYDIAAVAF RGRSACINFA DSAWKLPTPA SSDPKDIQKA AAEAAEAFRP LESEGVHSAG EESKEESTTP ETAESMYFMD EEALFCMPGL LANMAEGLML PPPQCSEVGD HFMEADADMP LWSYSV |
| PETCBF2.1 | 49 | MDIFGSYYSD ILPIELPEYS SPMSDNSSCS NYRANHSDDE VMLASNNPKK CAGRKKFRET RHPVYRGVRK RNGKWVCEVR EPNKKSRIWL |

FIGURE 3I

| Primer | SEQ ID NO: | Sequence |
|---|---|---|
|  |  | GSFPTAEMAA VAHDVAAIKL RGPDALTNFA DSAWKLPIPA SSNPKDIQKA AAEAAKAFRE SGEESKEESS TRETPEKMFF MDEEALFCMP ELLANMAEGL MLPPPSQCSD VGEHFMDADV DMPLWSYSI |
| PETCBF2.2 | 50 | MDIFGSYYSD ILPIELPEYS SPMSDNSSCS NYRANHSDDE VMLASNNPKK CAGRKKFRET RHPVYRGVRK RNGKWVCEVR EPNKKSRIWL GSFPTAEMAA LAHDVAAIKL RGPDALTNFA DSAWKLPIPA SSNPKDIQKA AAEAAKAFRE SGEESKEESS TRETPEKMFF MDEEALFCMP ELLANMAEGL MLPPPSQCSD VGEHFMDADV DMPLWSYSI |
| PETCBF2.3 | 51 | MDIFGSYYSD ILPIELPEYS SPMSDNSSCS NYRANHSDDE VMLASNNPKK CAGRKKFRET RHPVYRGVRK RNGKWVCEVR EPNRKSRIWL GSFPTAEMAA KAYDIAAVAL RGRSACINFA DSAWKLPIPA SSNPKDIQKA AAEAAKAFRE SGEESKEESS TRETPEKMFF MDEEALFCMP ELLANMAEGL MLPPPSQCSD VGEHFMDADV DMPLWSYSI |
| PETCBF3.1 | 52 | MDIFARYYSD QLPIASAATF WPLEVAEYSS PMSDISNNRA NLSDEEVMLA SNNPKKRAGR KKFQETRHPV YRGVRKRSSG KWVCEVREPN KKSRIWLGTY ITAEMAALAH DVAAIKLRGP DALTNFADSA WKLHIPASSK AKDIQKAATE AASAFQESKE EGTTPETPEK MLFMDEEALF YMPGLLANMA EGLMLPLPPQ CSEVGDHFME AAADMPLWSY SF |
| PETCBF3.2 | 53 | MDIFARYYSD QLPIASAATF WPLEVAEYSS PMSDISNNRA NLSDEEVMLA SNNPKKRAGR KKFQETRHPV YRGVRKRSSG KWVCEVREPN KKSRIWLGTY ITAEMAAVAH DVAAIKLRGP DALTNFADSA WKLHIPASSK AKDIQKAATE AASAFQESKE EGTTPETPEK MLFMDEEALF YMPGLLANMA EGLMLPLPPQ CSEVGDHFME AAADMPLWSY SF |
| PETCBF3.3 | 54 | MDIFARYYSD QLPIASAATF WPLEVAEYSS PMSDISNNRA NLSDEEVMLA SNNPKKRAGR |

FIGURE 3J

| Primer | SEQ ID NO: | Sequence |
|---|---|---|
| | | KKFQETRHPV YRGVRKRSSG KWVCEVREPN RKSRIWLGTY ITAEMAAKAH DIAAVALRGR SACINFADSA WKLHIPASSK AKDIQKAATE AASAFQESKE EGTTPETPEK MLFMDEEALF YMPGLLANMA EGLMLPLPPQ CSEVGDHFME AAADMPLWSY SF |
| PETCBF3.4 | 55 | MDIFARYYSD QLPIASAATF WPLEVAEYSS PMSDISNNRA NLSDEEVMLA SNNPKKRAGR KKFQETRHPV YRGVRKRSSG KWVCEVREPN KKSRIWLGTY ITAEMAAKAY DIAAVALRGR SACINFADSA WKLHIPASSK AKDIQKAATE AASAFQESKE EGTTPETPEK MLFMDEEALF YMPGLLANMA EGLMLPLPPQ CSEVGDHFME AAADMPLWSY SF |
| PETCBF4.1 | 56 | MDIFGRYYSD QLPIASAATF WPLEVAEYSD NSSSSSNNRA NVSDEEVMLA SNNPKKRAGR KKFQETRHPV YRGVRKRNSG KWVCEVREPN KKSRIWLGTY STAEMAALAH DRAAIKLRGP DALTNFADSA WKLPIPASSK AKDIQKAATE AAATAFLEPG EPETRKKNML FMDEEALFCM PGLLANMAEG LMLTPPQCYG EHFMEADAEV PLWSY |
| PETCBF4.2 | 57 | MDIFGRYYSD QLPIASAATF WPLEVAEYSD NSSSSSNNRA NVSDEEVMLA SNNPKKRAGR KKFQETRHPV YRGVRKRNSG KWVCEVREPN KKSRIWLGTY STAEMAAVAH DRAAIKLRGP DALTNFADSA WKLPIPASSK AKDIQKAATE AAATAFLEPG EPETRKKNML FMDEEALFCM PGLLANMAEG LMLTPPQCYG EHFMEADAEV PLWSY |
| PETCBF4.3 | 58 | MDIFGRYYSD QLPIASAATF WPLEVAEYSD NSSSSSNNRA NVSDEEVMLA SNNPKKRAGR KKFQETRHPV YRGVRKRNSG KWVCEVREPN KKSRIWLGTY STAEMAALAH DIAAIKLRGP DALTNFADSA WKLPIPASSK AKDIQKAATE AAATAFLEPG EPETRKKNML FMDEEALFCM PGLLANMAEG LMLTPPQCYG EHFMEADAEV PLWSY |
| PETCBF4.4 | 59 | MDIFGRYYSD QLPIASAATF WPLEVAEYSD |

FIGURE 3K

| Primer | SEQ ID NO: | Sequence |
|---|---|---|
| | | NSSSSSNNRA NVSDEEVMLA SNNPKKRAGR KKFQETRHPV YRGVRKRNSG KWVCEVREPN KKSRIWLGTY STAEMAAVAH DIAAIKLRGP DALTNFADSA WKLPIPASSK AKDIQKAATE AAATAFLEPG EPETRKKNML FMDEEALFCM PGLLANMAEG LMLTPPQCYG EHFMEADAEV PLWSY |
| PETCBF4.5 | 60 | MDIFGRYYSD QLPIASAATF WPLEVAEYSD NSSSSSNNRA NVSDEEVMLA SNNPKKRAGR KKFQETRHPV YRGVRKRNSG KWVCEVREPN RKSRIWLGTY STAEMAAKAH DIAAVALRGR AACINFADSA WKLPIPASSK AKDIQKAATE AAATAFLEPG EPETRKKNML FMDEEALFCM PGLLANMAEG LMLTPPQCYG EHFMEADAEV PLWSY |
| PETCBF4.6 | 61 | MDIFGRYYSD QLPIASAATF WPLEVAEYSD NSSSSSNNRA NVSDEEVMLA SNNPKKRAGR KKFQETRHPV YRGVRKRNSG KWVCEVREPN KKSRIWLGTY STAEMAAKAY DIAAVALRGR AACINFADSA WKLPIPASSK AKDIQKAATE AAATAFLEPG EPETRKKNML FMDEEALFCM PGLLANMAEG LMLTPPQCYG EHFMEADAEV PLWSY |

FIGURE 3L

PLANTS EXPRESSING ENVIRONMENTAL STRESS TOLERANCES HAVING PETUNIA CBF GENES THEREIN

This invention was made, at least in part, with government support under USDA-ARS Grant NO: 512009. The U.S. government has certain rights in the invention.

FIELD OF INVENTION

This invention relates to stress tolerance in plants. In addition, this invention relates to transcription factors and gene expression involved in stress tolerance in plants.

BACKGROUND

Cold, salinity, and drought restrict the range available for crop production. Corn production serves as an example. Within the United States, corn is cultivated in 26 states. The northern most boundary of corn production is within North Dakota and Minnesota and the western extreme is in Colorado. Even within this area states such as South Dakota are affected by drought, leading to low yields. Outside of this area, drought prohibits substantial cereal cultivation in states such as Arizona.

Similarly, in Canada there are risks associated with extending corn acreage. Last year alone corn production declined nearly 7.0% in the prairie provinces largely due to above average temperatures and dry conditions. The inability to effectively manage these environmental challenges is partially responsible for 96% of Canadian corn production remaining in Quebec and Ontario. This fact coupled with depression of feed prices in the prairie provinces, make expanded corn cultivation particularly risky in areas in Canada where unpredictable environmental challenges abide.

Crop production must meet the needs of the population, but population increases are expected worldwide. Population increases will be most significant in the developing nations where growth of 3.6%, 3.0%, 2.1% and 2.0% are expected in the southern Mediterranean, in the sub-Sahara, in the central Asian republics, and on the Indian subcontinent respectively. With population increases, the demand for crops will increase in developing nations. In contrast, drought reduces the annual corn harvest by 20 million tons and is second only to soil infertility as a constraint on corn production in the developing world.

Environmental stresses not only restrict corn production, but all crops are restricted. In addition crops are required not only for food, but for other products such as fuel, animal feed, paper, food additives, et cetera. A need exists to extend the range of crop production.

C-repeat Factors (CBFs) or Dehydration Responsive Element factors (DREB1s) are transcription factors, which induce several genes which in turn confer tolerance to freezing temperatures, drought, or salinity stresses in plants (Jaglo-Ottosen et al. (1998) Science, 280(5360): 104-6; Kasuga et al. (1999) Nat. Biotechnol. 17(3): 287-91). Various reported DREB1s are expressed differently depending on the nature of the stress to which the plant is exposed. Table 1 lists CBF genes and their induction pattern in response to environmental stress. DREB1D and DREB1F were reported to be induced only by salinity stress in the roots of *Arabidopsis* (Sakuma et al. (2002) Biochem. Biophy. Res. Commun. 290 (3): 998-1009). While rice OsDREB1A is induced by cold and salinity stresses (Dubouzet et al. (2003) Plant J. 33(4): 751-63), and *Arabidopsis* CBF4 is only induced by drought stress (Haake et al. (2002) Plant Physiol. 130(2): 639-48).

CBF genes induced by cold treatment at 4° C. have been reported (Gimour et al. (1998) Plant J. 6(4): 433-42, Liu et al. (1998) Plant Cell. 10(8): 1391-406, Medina et al. (1999) Plant Physiol. 119(2): 463-70, Gao et al. (2002) Plant Mol. Biol. 49(5): 459-71). In *Arabidopsis* cold induced CBF genes are uniformly and highly induced upon cold stress. However, in previously reported CBF cold tolerance cases, transgenic plants constitutively overexpressing CBF genes are stunted and the severity of stunting positively correlates with the level of CBF gene expression in the transgenic plants (Liu et al. (1998) Plant Cell. 10(8): 1391-406). Other CBF genes and their expression profiles are discussed in Chen et al. (2003) Theor. Appl. Genet. 107(6): 971-9; Choi et al. (2002) Plant Physiol. 129(4): 1781-7; Jaglo et al. (2001) Plant Physiol. 127(3): 910-7; Qin et al. (2004) Plant Cell Physiol. 45(8): 1042-52; and Zhang et al. (2004) Plant J. 39(6): 905-19. Each of the above references is incorporated by reference as if fully set forth herein.

TABLE 1

CBF/DREB1 Genes and their Induction Pattern

| CBF Gene | Induced by | | |
|---|---|---|---|
| | Cold | Drought | Salinity |
| *Arabidopsis* CBF1 | • | ○ | — |
| *Arabidopsis* CBF2 | • | ○ | — |
| *Arabidopsis* CBP3 | • | ○ | — |
| *Arabidopsis* DREB1A | • | ○ | ○ |
| *Arabidopsis* DREB1B | • | ○ | ○ |
| *Arabidopsis* DREB1C | • | ○ | ○ |
| *Arabidopsis* CBF1 | • | ○ | — |
| *Arabidopsis* CBF2 | • | ○ | — |
| *Arabidopsis* CBF3 | • | ○ | — |
| *Brassica* BnCBF | • | — | — |
| Rye ScCBF | • | — | — |
| Wheat CBF TaCBF | • | — | — |
| Tomato CBF LeCBF | • | — | — |
| Barley HvCBF3 | • | — | — |
| *Brassica* BNCBF5 | • | ○ | — |
| *Brassica* BNCBF7 | • | ○ | — |
| *Brassica* BNCBF16 | • | ○ | — |
| *Brassica* BNCBF17 | • | ○ | — |
| *Arabidopsis* DREB1D | ○ | ○ | • |
| *Arabidopsis* DREB1E | ○ | ○ | ○ |
| *Arabidopsis* DREB1F | ○ | ○ | • |
| *Arabidopsis* CBF4 | ○ | • | ○ |
| Rice OsDREB1A | • | ○ | • |
| Rice OsDREB1B | • | ○ | ○ |
| Rice OsDREB1D | ○ | ○ | — |
| Rice OsDREBL | • | ○ | ○ |
| Tomato LeCBF1 | • | ○ | ○ |
| Tomato LeCBF2 | ○ | ○ | ○ |
| Tomato LeCBF3 | ○ | ○ | ○ |
| *Petunia* ZmBREB1A | • | — | — |

[Legend: • Induced; ○ Not Induced; — Not known]

There is a need for control of stress tolerance in plants that includes differential response to various stresses, including cold temperatures. There is also a need for producing stress tolerance in plant which does not result in deleterious traits such as stunting. In addition, there is a need for control of stress response in plants which extends not only to one or two environmental stresses, but to at least three.

SUMMARY

In one aspect, the present invention relates nucleic acids comprising sequences having at least 72% identity with SEQ ID NO: 27, SEQ ID NO: 28, SEQ ID NO: 29 SEQ ID NO: 30, SEQ ID NO: 40, SEQ ID NO: 41, SEQ ID NO: 42 or SEQ ID NO: 43. The present invention also relates to vectors comprising these nucleic acids.

In another aspect, the present invention relates to nucleic acids comprising sequences that hybridize under moderate stringency conditions with the complement of nucleic acids having the sequence of SEQ ID NO: 27, SEQ ID NO: 28, SEQ ID NO: 29 SEQ ID NO: 30, SEQ ID NO: 40, SEQ ID NO: 41, SEQ ID NO: 42 or SEQ ID NO: 43. The present invention also relates to vectors comprising these nucleic acids.

In another aspect, the present invention relates to nucleic acids comprising a nucleotide sequence encoding a protein having the amino acid sequence with at least 72% identity to one of sequences of SEQ ID NOS: 32-35 and 44-61. The present invention also relates to vectors comprising these nucleic acids.

In another aspect, the present invention relates to proteins expressed from a nucleic acid comprising a sequence that hybridizes under conditions of moderate stringency with the complement of nucleic acids having the sequence of SEQ ID NO: 27, SEQ ID NO: 28, SEQ ID NO: 29, SEQ ID NO: 30, SEQ ID NO: 40, SEQ ID NO: 41, SEQ ID NO: 42 or SEQ ID NO: 43.

In another aspect, the present invention relates to proteins having an amino acid sequence with at least 72% identity to the sequences of SEQ ID NOS: 32-35 and 44-61.

In another aspect, the present invention relates to plants transformed with a nucleic acid comprising a sequence having at least 72% identity with the sequence of SEQ ID NO: 27, SEQ ID NO: 28, SEQ ID NO: 29, SEQ ID NO: 30, SEQ ID NO: 40, SEQ ID NO: 41, SEQ ID NO: 42 or SEQ ID NO: 43.

In another aspect, the present invention relates to transgenic plants comprising a nucleic acid that hybridizes under conditions of moderate stringency to the complement of nucleic acids having the sequence of SEQ ID NO: 27, SEQ ID NO: 28, SEQ ID NO: 29, SEQ ID NO: 30, SEQ ID NO: 40, SEQ ID NO: 41, SEQ ID NO: 42 or SEQ ID NO: 43.

In another aspect, the present invention relates to transgenic plants comprising a nucleic acid that hybridizes under conditions of moderate stringency to a nucleic acid having the sequence of SEQ ID NO: 40, SEQ ID NO: 41, SEQ ID NO: 42 or SEQ ID NO: 43.

In another aspect, the present invention relates to transgenic plants comprising a protein having an amino acid sequence that has at least 72% identity with the sequence of SEQ ID NOS: 32-35 and 44-61.

In another aspect, the present invention relates to methods of producing a plant having a modified tolerance to environmental stress including the step of providing a vector having a nucleic acid with at least 72% identity to the sequences selected from the group consisting of SEQ ID NO: 27, SEQ ID NO: 28, SEQ ID NO: 29, SEQ ID NO: 30, SEQ ID NO: 40, SEQ ID NO: 41, SEQ ID NO: 42, or SEQ ID NO: 43 to the plant.

In another aspect, the present invention relates to methods for producing increased yields per acre. The methods include transforming a plant with a nucleic acid having a sequence with at least 72% identity to the sequences SEQ ID NO: 27, SEQ ID NO: 28, SEQ ID NO: 29, SEQ ID NO: 30, SEQ ID NO: 40, SEQ ID NO: 41, SEQ ID NO: 42, or SEQ ID NO: 43. The seed from the transformed plant are isolated and planted. Recombinant plants are then grown from the seed, and biomass produced by the recombinant plants is harvested.

In another aspect, the invention relates to methods of expressing an exogenous gene in a plant. The methods include cloning the exogenous gene into a nucleic acid containing regulatory elements controlled by the expression of PetCBF1, PetCBF2, PetCBF3 or PetCBF4. The cloned exogenous gene is provided to a plant containing a sequence with at least 72% identity with a sequence selected from the group consisting of SEQ ID NO: 27, SEQ ID NO: 28, SEQ ID NO: 29, and SEQ ID NO: 30, and the plant is exposed to environmental stress.

In another aspect, the invention relates to methods of expressing an exogenous gene in a plant. The methods include cloning the exogenous gene into a nucleic acid such that the exogenous gene is operably connected to a sequence having at least 72% identity with a sequence from the group consisting of SEQ ID NO: 36, SEQ ID NO: 37, SEQ ID NO: 38, and SEQ ID NO: 39. The cloned exogenous gene is provided to a plant, and the plant is exposed to environmental stress.

In another aspect, the invention relates to isolated nucleic acids comprising a fragment of at least 8 nucleotides of a sequence with at least 90% identity with a sequence from SEQ ID NO: 27, SEQ ID NO: 28, SEQ ID NO: 29, or SEQ ID NO: 30.

In another aspect, the invention relates to isolated amino acid sequences comprising a fragment of at least 8 amino acids of a sequence with at least 90% identity with a sequence from SEQ ID NOS: 32-35 and 33-61.

In another aspect, the invention relates to promoters having sequences with at least 72% identity with the sequence of SEQ ID NO: 36, SEQ ID NO: 37, SEQ ID NO: 38 or SEQ ID NO: 39.

BRIEF DESCRIPTION OF THE DRAWING(S)

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

Figure 1:
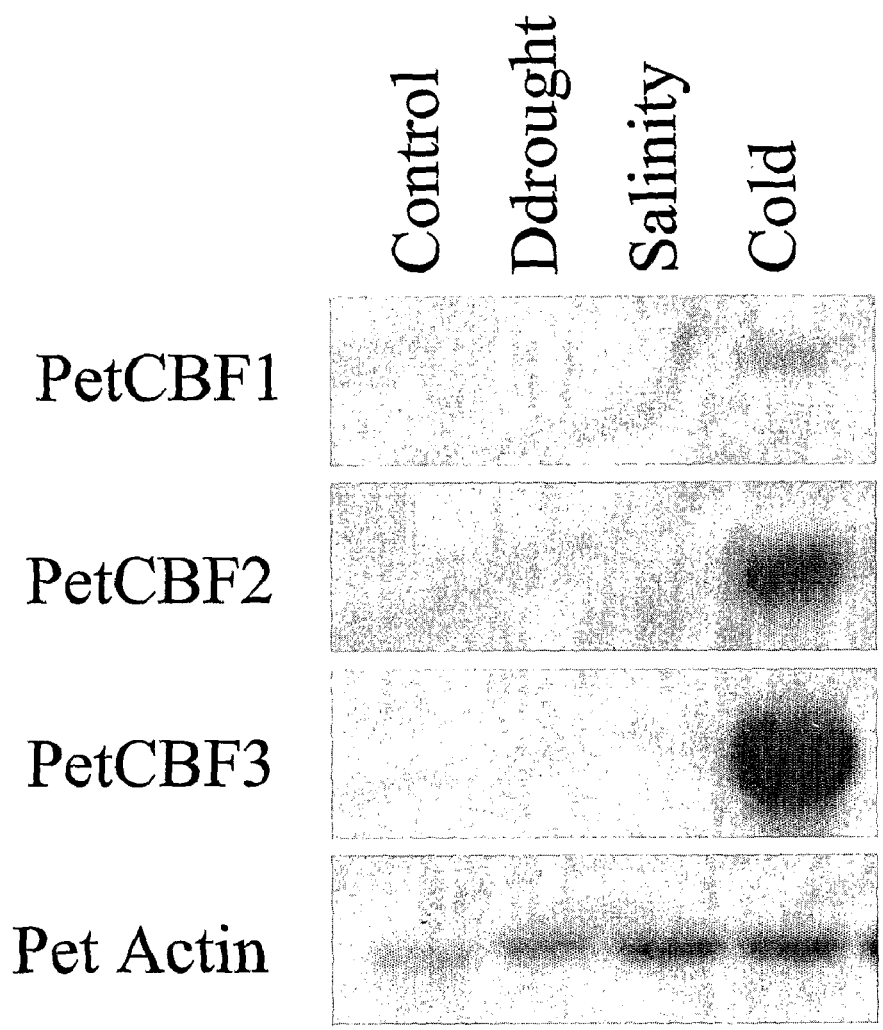
FIG. 1 illustrates Northern blot analysis of the expression of PetCBF1, PetCBF2 and PetCBF3 genes in *Petunia hybrida* v26.

FIG. 3, including FIGS. 3A to 3L illustrates embodiments of nucleic acid and amino acid sequences of the invention.

DETAILED DESCRIPTION OF THE PREFERRED EMBODIMENT(S)

Certain terminology is used in the following description for convenience only and is not limiting. The words "right," "left," "top," and "bottom" designate directions in the drawings to which reference is made.

"Gene of interest" is understood by one of ordinary skill in the art and may include homologous DNA, heterologous DNA, foreign DNA, genomic DNA or cDNA.

"Identity" or "Sequence Identity" in reference to a nucleic acid is the percent of nucleotides in a given sequence that are the same as the corresponding nucleotides in a reference sequence. "Identity" or "Sequence Identity" in reference to a protein is the percent of amino acid residues in a given sequence that are the same as the corresponding amino acid residues in a reference sequence.

As used herein, the designation "variant" denotes a molecule that retains a biological activity (either function or structural) that is substantially similar to that of the original sequence. The variant may be from the same or different species and may be a natural variant or be prepared synthetically.

The term "derivative" is intended to include any of the described variants that have been used for the purpose of labeling, or comprise a fusion product(s).

The term "fragment" refers to any segment of an identified DNA, RNA or amino acid sequence and/or any segment of any of the variants or derivatives described in the above definitions.

All nucleic acids, nucleotide sequence, proteins or amino acid sequences referred to herein can be isolated, purified, synthesized chemically, or produced through recombinant DNA technology. All of these methods are well known in the art.

As used herein "environmental stress" includes, but is not limited to, cold, dehydration, and salinity. Cold temperatures can include freezing and above freezing, and below freezing temperatures.

As used herein, "environmental stress tolerance genes" refer to genes which function to acclimatize a plant to an environmental stress. For example, cold tolerance genes refer to genes which function to acclimatize a plant to a cold temperature environment. Dehydration tolerance genes refer to genes which function to acclimatize a plant to dehydration stress. It is noted that some cold tolerance genes may function to provide a plant with a degree of dehydration tolerance and visa versa. For example, some cold tolerance genes are activated by dehydration stress also. The present invention encompasses genes which regulate one or more environmental stress tolerance genes such as cold tolerance genes, dehydration tolerance genes, and genes, which perform a dual function of cold and dehydration tolerance.

As used herein "coding region" refers to the region of a nucleic acid that codes for an amino acid sequence.

As used herein, "transformed" or "transfrom" indicates any method of introducing a nucleic acid into a host including, but not limited to, transformation, transduction, transfection, electroporation, and biolistic methods.

As used herein, "host" denotes any cell, tissue, organ or non-human organism in which a nucleic acid or protein can be introduced or exists.

As used herein, "exogenous gene," "exogenous nucleic acid," "exogenous protein," or "exogenous amino acid sequence" (collectively, exogenous "biomolecule") indicates that the identified biomolecule is not originally isolated from the individual host in which it is introduced or expressed. A bimolecule may be "exogenous" even if an identical or similar biomolecule exists in the host in which the biomolecule is introduced or expressed.

The words "a," "and," "one," as used in the claims and in the corresponding portions of the specification, are defined as including one or more of the referenced item unless specifically stated otherwise. This terminology includes the words above specifically mentioned, derivatives thereof, and words of similar import.

Figure 2:
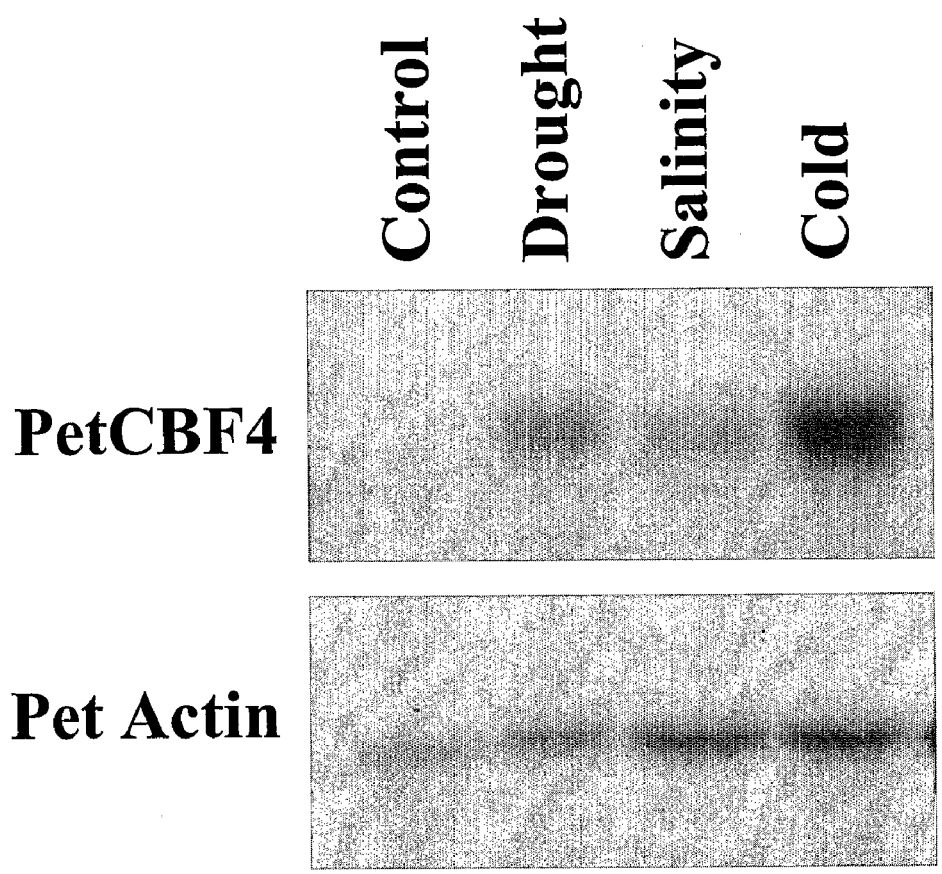
FIG. 2 illustrates Northern blot analysis of the expression of the PetCBF4 gene in *Petunia hybrida* v26.

Embodiments of the present invention provide for the identification, isolation, sequencing and characterization of three CBF genes from *Petunia hybrida* v26, which are differentially induced upon exposure to cold temperature. Each of these genes possesses a reproducible and characteristic level of expression under cold temperatures. Referring to FIG. 1, PetCBF1 [SEQ ID NO: 27], PetCBF2 [SEQ ID NO: 28], and PetCBF3 [SEQ ID NO: 29] are differentially expressed upon cold treatment at 4° C. As illustrated, mRNA expression levels are low, medium and high for PetCBF [SEQ ID NO: 27], PetCBF2 [SEQ ID NO: 28], and PetCBF3 [SEQ ID NO: 29], respectively. Referring to FIG. 2, PetCBF4 [SEQ ID NO: 30] is induced by three different stresses; cold, drought and salinity. PetCBF1, PetCBF2, PetCBF3 and PetCBF4 genes of the present invention have 34 to 51% nucleotide identity with CBF genes cloned from *Arabidopsis*. By modulating the expression level of PetCBF in response to cold using one or a combination of these genes, the link between cold tolerance and stunted growth can be broken.

In a preferred embodiment, nucleic acids of the present invention include the full length sequences of PetCBF1 [SEQ ID NO: 27], PetCBF2 [SEQ ID NO: 28], PetCBF3 [SEQ ID NO: 29] and PetCBF4 [SEQ ID NO: 30]. In another preferred embodiment, the nucleic acids of the invention include the open reading frames of PetCBF1-4, i.e. PetCBF1 ORF [SEQ ID NO: 40], PetCBF2 ORF [SEQ ID NO: 41], PetCBF3 ORF [SEQ ID NO: 42] and PetCBF4 ORF [SEQ ID NO: 43]. In yet another preferred embodiment the promoters of the PetCBF1-4 genes are provided, i.e. SEQ ID NO: 36, SEQ ID NO: 37, SEQ ID NO: 38, and SEQ ID NO: 39. In still another embodiment of the invention variants of the above nucleic acids are provided. In particularly preferred embodiments, nucleic acids which encode an amino acid sequence comprising SEQ ID NOS: 44-61 are provided. Nucleic acids of the present invention are generically referred to as PetCBF gene(s), PetCBF DNA, PetCBF RNA, PetCBF nucleic acid, PetCBF sequence or PetCBF herein.

Embodiments of invention include nucleic acid variants which in turn include substitutions, deletions or additions of one or more nucleotides, provided that the biological activity (structural or functional) of the sequence is generally maintained. Also provided are nucleic acids comprising at least 8 nucleotides, at least 15 nucleotides, at least 25 nucleotides, at least 50 nucleotides, at least 100 nucleotides, at least 200 nucleotides, at least 350 nucleotides, or at least 550 nucleotides of a PetCBF DNA or RNA. In various embodiments, PetCBF nucleic acids are provided that are less than full length, less than 1,000, less than 500, less than 275, less than 200, less than 100, or less than 50 bases (or bp, if double-stranded). In an embodiment, the nucleic acids of the invention may include fragments of the PetCBF nucleic acids in segments of contiguous 10 nucleotides, i.e. nucleotide sequences comprising nucleotides 1-10, 10-20, 20-30. In further embodiments, the 10 nucleotide segments may be combined, i.e. nucleotide sequences may comprise nucleotides 1-10, 1-20, 1-30, 20-30, 20-40, 30-50, 30-100, or any combinations of the 10 nucleotide sequences that comprise up to all of a PetCBF gene, including coding or regulatory regions or a PetCBF RNA. Nucleic acids can be single-stranded or double-stranded. In another embodiment, isolated nucleic acids are provided that comprise at least 15 contiguous nucleotides of PetCBF coding sequences.

Embodiments of the invention also provide single-stranded oligonucleotides for use as primers in PCR. PCR primers of the present invention include an oligonucleotide having the sequence of a hybridizable portion (at least about 8 nucleotides) of a PetCBF nucleic acid, and another oligonucleotide having the reverse complement of a downstream sequence in the same strand of the PetCBF gene, such that each oligonucleotide primes synthesis in a direction toward the other. The oligonucleotides are preferably in the range of 10-35 nucleotides in length.

Embodiments of the present invention also provide nucleic acids hybridizable to or complementary to the above-described nucleic acids comprising PetCBF sequences. In specific embodiments, nucleic acids are provided which comprise a sequence complementary to at least 8, 10, 25, 50, 100, or 200 nucleotides, the entire coding region of a PetCBF gene, or an entire PetCBF gene. In a specific embodiment, a nucleic acid which is hybridizable to a PetCBF nucleic acid, or to a nucleic acid encoding a PetCBF variant, under conditions of low stringency is provided. By way of example and not limitation, procedures using such conditions of low stringency are as follows (see also Shilo and Weinberg, 1981, Proc. Natl. Acad. Sci. USA 78:6789-6792 which is hereby incorporated by reference as if fully set forth): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe are used. Filters are incubated in hybridization mixture for 18-20 h at 40° C. and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and reexposed to film.

Embodiments of the present invention also provide a nucleic acid which is hybridizable to a PetCBF nucleic acid, or to a nucleic acid encoding a PetCBF variant, under conditions of high stringency. By way of example and not limitation, "high stringency" as used herein refers hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium pyrophosphate), 5×Denhardt's solution, sonicated salmon sperm DNA (50 g/ml), 0.1% SDS, and 10% dextran sulfate at 42° C., with washes at 42° C. in 0.2×SSC and 0.1% SDS.

In another embodiment, a nucleic acid which is hybridizable to a PetCBF nucleic acid or variant under conditions of moderate stringency is provided. One of ordinary skill in the art will recognize that moderate stringency lies between low and high stringency. For example, moderate stringency includes hybridizing in 3×SSC at 42° C. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.), both of which are hereby incorporated by reference as if fully set forth.

A preferred embodiment includes a PetCBF nucleic acid variant sharing at least 72% nucleotide sequence identity to the naturally occurring PetCBF gene. A particularly preferred PetCBF nucleic acid variant is one sharing at least 82% nucleotide sequence identity and another particularly preferred PetCBF nucleic acid variant is one sharing at least 90% nucleotide sequence identity to a nucleic acid having the sequence of one of SEQ ID NOS: 27-30 and 40-43. In another embodiment, a PetCBF nucleic acid variant is one that shares the foregoing percentages of sequence identity over at least 25, at least 50, at least 75, at least 100, at least 200, at least 300, at least 500, at least 1000, or at least the full-length contiguous nucleotides of the PetCBF nucleic acid.

Embodiments of the present invention include proteins encoded by SEQ ID NO: 27, SEQ ID NO: 28, SEQ ID NO: 29, SEQ ID NO: 30, SEQ ID NO: 40, SEQ ID NO 41, SEQ ID NO: 42, SEQ ID NO: 43 or SEQ ID NO: 44. The proteins of the present embodiments also include the amino acid sequences of SEQ ID NO: 32, SEQ ID NO: 33, SEQ ID NO: 34, and SEQ ID NO: 35. Other embodiments include proteins comprising the amino acid sequence of one of SEQ ID NOS: 44-61. In yet other embodiments the present invention provides protein variants. Protein variants include PETCBF amino acid sequences, derivatives or fragments having substitutions, deletions, or additions of one or more amino acids, provided that the biological activity of the amino acid sequence, derivative or fragment is conserved. The variants of these embodiments include, but are not limited to, those containing, as a primary amino acid sequence, all or part of the amino acid sequence of a PETCBF protein, and derivatives or fragments including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. Exemplary classes of amino acids include the following. The nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Another embodiment of the present invention provides fragments of a PETCBF protein consisting of at least 8 amino acids, at least 10 amino acids, at least 25 amino acids, at least 50 amino acids, or at least 100 amino acids. Nucleic acids encoding such fragments are also within the scope of the invention. A preferred PETCBF protein variant is one sharing at least 72% amino acid sequence identity, a particularly preferred PETCBF protein variant is one sharing at least 82% amino acid sequence identity and another particularly preferred PETCBF protein variant is one sharing at least 90% amino acid sequence identity to the naturally occurring PETCBF protein over at least 25, at least 50, at least 75, at least 100, or at least the full-length contiguous amino acids of the reference PETCBF amino acid sequence. In another embodiment, a PETCBF variant protein is one that shares the foregoing percentages of sequence identity over the recited lengths of amino acids. Proteins encoded by nucleic acids hybridizable to a PetCBF gene under low stringency, moderate stringency, or high stringency conditions are also provided.

Nucleic acid or protein variants of PetCBF1-4 nucleic acids or PETCBF1-4 amino acid sequences can be identified using methods routine in the art. In one embodiment variants that retain biological function are identified by the physiologic response of a plant, plant tissue, or plant cell containing the variant. Known physiologic responses to CBF genes are described in Gilmore et al. (2002) Plant Physiol. 124: 1854-1865; and Gilmore et al. (2004) Proc. Natl. Acad. Sci. 101: 15243-15248, both of which are incorporated by reference as if fully set forth. In particular, elevated proline, soluble sugars (sucrose, raffinose, glucose, glucose-6-phosphate, lactose, fructose, fructose-6-phosphate, and fructose-1,6-phosphate), elevated P5CS (A1-pyrolline 5-carboxylate synthase) transcripts and associated increases in P5CS, or increased levels of A1 pryolline 5-reductase are indicative of CBF biological function. Also, elevated levels of transcripts or proteins associated with proline, glycine, or betain biosynthesis are indicative of CBF biological function. All of these products are detectable using standard methods known in the art.

Variants may also be identified by response to environmental stress. Plants, plant tissue, or plant cells containing a candidate variant may be exposed to environmental stress and their response in relation to controls can be scored. Those samples that exhibit increased tolerance corresponding to a particular PetCBF or PETCBF display the biological function. The candidate variant is thus an embodiment of the invention.

In another embodiment, the DNA sequences of the present invention, including SEQ ID NOS: 27, 28, 29 and 30, may be covalently linked to a vector, and therefore, can include sequences unrelated to the gene sequence encoding the protein. Suitable vectors of the preferred embodiments include, but are not limited to pUC plasmids, pBR322 and related plasmids, pACYC and related plasmids, transcription vectors, expression vectors, phagemids, yeast expression vectors, plant expression vectors, pDONR201 (Invitrogen), pBI121, pBIN20, pEarleyGate100 (ABRC), pEarleyGate102 (ABRC), pCAMBIA, T-DNA, transposons, and artificial chromosomes. In preferred embodiments the vector is capable of being transformed into a host.

In some embodiments DNA sequences of the present invention may be operably linked to a promoter or other regulatory elements such as enhancers or operators. Promoters contemplated under these embodiments include, but are not limited to lac promoters, tac promoters, cat promoters, constitutive promoters, inducible promoters, temperature sensitive promoters, and tissue specific promoters including flower, fruit or seed specific promoters. Promoters of preferred embodiments include P5CS, OCS, Maize cat, GSTG, 35S, Rd29A, Maize ubiquitin, Maize actin, and rice ubiquitin promoters. A sequence operably linked to a promoter is expressed under the control of the promoter. In a preferred embodiment the promoter is activated when exposed to temperatures equal to or less than 20° C. and thereby induces expression of operably linked sequences at said temperatures. Particularly preferred embodiments include the promoters of SEQ ID NO: 36, SEQ ID NO: 37, SEQ ID NO: 38 and SEQ ID NO: 39.

The regulatory elements or promoters of the present invention may be used to regulate gene expression. Regulation of expression can include causing one or more stress tolerance genes to be expressed under different conditions than those genes would be in the plant's native state, increasing a level of expression of a stress tolerance genes, or causing the expression of one or more stress tolerance genes to be inducible by an exogenous agent. Expression can be under the control of a variety of promoters. In certain embodiments, promoters can be used to overexpress the protein, change the environmental conditions under which the protein is expressed, or enable the expression of the protein to be induced, for example by the addition of an exogenous inducing agent. Promoters can also be used to cause the protein to be expressed at selected times during a plant's life. Tissue-specific promoters can be used to cause the protein to be expressed in selected tissues. For example, flower-, fruit- and seed-specific promoters can be used to cause the protein to be selectively expressed in flowers, fruits or seeds of the plant.

In another embodiment, exogenous genes may be cloned into regions of a genome controlled by the expression of PetCBF genes. Since PetCBF genes are transcription factors, numerous genes within a genome may be expressed in response to the expression of PetCBF genes. An exogenous gene cloned into regions of a genome controlled by PetCBF genes could be expressed upon exposure to the stress conditions. In a further embodiment, the promoters that drive expression of the PetCBF gene may be replaced by any other desired promoter. In this embodiment, exogenous gene expression system is controlled by the other promoter.

In another embodiment, the coding region of a PetCBF gene of the present inventions is replaced in part or total with an exogenous gene. The exogenous gene may then be expressed from a promoter controlling the PetCBF gene.

Embodiments of the present invention include PetCBF nucleic acid sequences transformed into a host. Accordingly, embodiments of the invention include transgenic cells, transgenic plants and transgenic plant materials (e.g., plant tissue, seeds) into which one or more gene sequences have been introduced. Additional embodiments include cells, plants and plant materials within which PetCBF sequences are expressed or subsequently modified. Suitable hosts of the present invention include but are not limited bacterium such as *Escherichia coli* and *Agrobacterium tumefaciens*. Other suitable hosts include yeast, for example *Saccharomyces cerevisiae*. In addition, suitable hosts may include plant cells, plant tissue or plants. In particular embodiments, plant cell or plant tissue hosts are derived from monocotyledons or dicotyledons and plant hosts include monocotyledons or dicotyledons. In preferred embodiments, the plant cell, plant tissue, or plant hosts may be derived from or include any of the following: petunia, soybean, wheat, corn, switchgrass, miscanthus, willow, poplar, potato, cotton, rice, oilseed rape, sunflower, alfalfa, clover, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, mint, labiates, rosaceous fruits, and vegetable brassicas.

Through introduction of the PetCBF nucleic acid, the PetCBF may reside within a host cell or be integrated within the host genome. Regardless of whether the PetCBF nucleic acid resides in any particular cellular compartment, or is covalently integrated with host nucleic acid, the PetCBF is incorporated in a host.

In principle any native or recombinant DNA molecule can be transferred to a plant cell and covalently linked to the resident chromosomal DNA. In a preferred embodiment a nucleotide sequence of the present invention (e.g., at least one of SEQ ID NOS: 27-30 and 36-43 or any variants at or greater than 52% homology) can be incorporated into an cassette to serve as either as a screenable, scorable or selectable marker. If these sequences are linked in cis to a second nucleic acid sequence that encodes a function associated with growth, pharmaceutic production, plant morphology, nutritional enhancement, biotic or abiotic challenge, chemical or environmental remediation, transformed cells can be distinguished from non-transformed cells, tissues, or plants following challenge to cold, drought, or salinity. Thus the sequences function to identify plants, tissues, or cells that incorporated second nucleic acid sequence.

A number of selectable markers have been employed to advance transformed cell identification. These include antibiotic resistant markers kanamycin (nptII), hygromycin B (aph IV) and gentamycin (aac3 and aacC4 and dominat plant selectable markers (hygromycin, kanamycin, bleomycin, G418, streptomycin or spectinomycin) in addition to the herbicide resistance marker phosphosphinothricin acetyltransferase. Use of these markers are well described in the literature.

Methods of nucleic acid engineering in any of the above embodiments are routine in the art. One of ordinary skill in the art would understand that any suitable method, for example those disclosed in Sambrook et al., 1989; or Ausubel et al., 1995, may be used to create the nucleic acids, amino acid sequences or proteins of the present invention.

Methods of creating transgenic plants are known in art. In general, a nucleic acid sequence is cloned into a vector and the vector is provided to a plant, plant tissue, plant seed, plant cells or the like through known methods of transformation. After providing the vector, plants are allowed to grow, and those with correct expression profile are selected. In one embodiment, the vector may include a selectable marker such as resistance to a deleterious agent and selection may include exposing plants to said agent. In another embodiment, selection may include exposing the plants to environmental stress and selecting those that are tolerant to the stress. Other embodiments may include combinations of selection schemes or criteria. If desired the selected plant(s) are allowed to grow to fertility and produce seeds. Recombinant seeds are then collected. In some embodiments the vector contains targeting sequences and regulatory elements sufficient to direct integration of the nucleic acids of the invention into a host genome.

A preferred embodiment utilizes *Agrobacterium tumefaciens* to create transgenic plants. The T-DNA of the Ti plasmid of *Agrobacterium tumefaciens* can be used to introduce modified genes into plants. However, the Ti plasmid is too large to manipulate easily in vitro. Strategies to overcome this difficulty utilize the hormone and opine synthesis genes in T-DNA. These genes are not necessary for replication or transfer of T-DNA and can be replaced by a gene of interest. The remaining vir genes of the Ti plasmid are located outside of this region and are still available to facilitate transfer of T-DNA.

In another preferred embodiment, a binary vector system, a plasmid containing the left and right borders of T-DNA is engineered to contain an exogenous gene of interest. If needed, an antibiotic resistance gene may be introduced in order to provide a basis of selecting transformed plant cells. Other genes conferring a selectable phenotype in the presence of an exogenous agent other than an antibiotic may also be utilized. The modified plasmid may be transformed into *E. coli* and then transferred by conjugation to an *A. tumefaciens* strain containing a helper plasmid. The helper plasmid provides the vir functions. On infection of a plant, the activated vir functions recognize the left border sequence of the modified plasmid and transfer all DNA between left and right borders to a plant chromosome.

In additional embodiments, transgenic plants may be created by biolistic methods, as known in the art.

In other embodiments, the proteins or amino acid sequences of the present invention are associated with a host. Associated with a host may include being incorporated in a host directly or expressed from a nucleic acid previously incorporated in a host. Suitable hosts include, but are not limited to those listed above with reference to the nucleic acids of the present invention.

Using the above methods a plant having modified tolerance to environmental stress may be produced. The plants so produced may be self crossed or crossed with another plant in order to produce seed and progeny. Progeny may be derived from growth from seed or any other means of propagating plants as understood by one of ordinary skill in the art. Embodiments of the invention also include cold or freezing temperature tolerant plants. In another embodiment, the present invention relates to novel plants that are genetically engineered to have the desirable traits for tolerance to cold or freezing temperatures, drought and salinity using a single gene. As a result, a single plant may withstand drought, cold temperatures, freezing temperatures, and salinity. In a preferred embodiment the single gene may be a gene comprising a nucleic acid including the sequence of SEQ ID NO: 30 or SEQ ID NO: 39. These embodiments also enable changing the planting date of crops in order to escape severe conditions, escape pathogens that correlate with sever conditions, to match harvest time with peak market demand for produce, or extend the growing area or season of a crop.

Expanded planting of transgenic grains, legumes etc. described under one or more of the embodiments herein may allow planting strategies that isolate transgenic seeds, grain, and plants, in order to prevent genetically engineered crops from entering the food chain. Specifically, the opportunity exists to designate defined geographic regions for transgenic crops expressing PetCBF genes which are drought, cold, or salinity resistant.

In yet another embodiment of the present inventions, the yield of biomass per acre may be increased by producing the plants of the present inventions, isolating the seed, planting the seed, growing the recombinant plants, and harvesting biomass produced. In a further embodiment, the yield per acre of biomass may be converted to secondary products such as, but not limited to textiles, food additives, fermentation products, e.g. ethanol, or the like. Thus the embodiments of the current invention include increasing the world's harvest.

EXAMPLES

Example 1

PetCBF Genes Differentially Induced by Cold Temperature in Plants

Isolation of PetCBF1-3

*Petunia hybrida* v26 seeds were sown in the pots and grown at 22° C. in the green house. Four-week-old plants were subjected to cold treatment at 4° C. for 3 h. Total RNA was isolated from leaf tissue of the treated plants by using TRI-ZOL reagent (Invitrogen, Carlsbad, Calif.), and purified using RNEASY Plant Mini Kit (Qiagen, Valencia, Calif.).

First strand cDNA was synthesized using total RNA as template and oligo-dT(18) as primer. From the first strand cDNA product, a fragment of 228 bp was amplified by PCR (Polymerase Chain Reaction) using degenerate primers (PetF4 [SEQ ID NO: 1] and PetR5 [SEQ ID NO: 2]).

The cDNA fragment was gel-eluted, cloned in pCR2.1-TOPO (Invitrogen, Carlsbad, Calif.), and fifteen randomly selected clones were sequenced. Based on the sequence information derived from these clones, three 3'RACE-PCR primers (3RACE1 [SEQ ID NO: 3], 3RACE2 [SEQ ID NO: 4], 3RACE3 [SEQ ID NO: 5]) and three 5'RACE-PCR primers (5RACE1 [SEQ ID NO: 6], 5RACE2 [SEQ ID NO: 7], 5RACE3 [SEQ ID NO: 8]) were designed.

Using these primers, RACE-PCR (Rapid Amplification of CDNA Ends-Polymerase Chain Reaction) was carried out using the SMART RACE cDNA Amplification Kit (BD Biosciences, Palo Alto, Calif.). The PCR products were cloned in pCR2.1-TOPO.

Of 30 clones sequenced, four were unique 5'RACE clones and four were unique 3'RACE clones. A forward primer from each of the 5'RACE clones (ParF1 [SEQ ID NO: 9], ParF2 [SEQ ID NO: 10], ParF3 [SEQ ID NO: 11], ParF4 [SEQ ID NO: 12]) and a reverse primer from each of the 3'RACE clones (ParR1 [SEQ ID NO: 13], ParR2 [SEQ ID NO: 14], ParR3 [SEQ ID NO: 15], ParR4 [SEQ ID NO: 16]) were designed for final RT-PCR.

These primers were used in all possible combinations, and PCR was carried out using the first strand cDNA as template. These PCR products were cloned in pCR2.1-TOPO and sequenced. Based on the sequence information, right combinations of 5RACE and 3RACE PCR clones were identified. Complete sequences of four distinct full-length cDNA clones were assembled.

Three such clones were obtained by using:

ParF3 [SEQ ID NO: 11] and ParR1 [SEQ ID NO: 13]; ParF4 [SEQ ID NO: 12] and ParR2 [SEQ ID NO: 14]; and, ParF1 [SEQ ID NO: 19] and ParR3 [SEQ ID NO: 15] were named as:

PetCBF1 [SEQ ID NO: 27], PetCBF2 [SEQ ID NO: 28], and PetCBF3 [SEQ ID NO: 29], respectively. The sequences of the primers used are given in Table 2.

Analysis of PetCBF1-3 Gene Expression

Cold treatment: *Petunia hybrida* v26 seeds were sown in the pots and grown at 22° C. in a green house. Four-week-old plants were subjected to cold treatment by placing them in a growth chamber set at 4° C. for 2 h.

Drought treatment: *Petunia hybrida* v26 seeds were sown in the pots and grown at 22° C. in the green house. Leaves from four-week-old plants were subjected to drought by detaching them from the plant and leaving at room temperature for 2 h.

Salinity treatment: *Petunia hybrida* v26 plants were hydroponically grown in nutrient solution. Four-week-old plants were subjected to salinity treatment by supplementing the nutrient solution with 250 mM sodium chloride.

Control: Four-week-old plants maintained at 22 C.

Northern hybridization: Probes specific for PetCBF1 gene were generated by PCR amplification of the 3'UTR region using CBF1ProbeF [SEQ ID NO: 17] and CBF1ProbeR [SEQ ID NO: 18]. Probes specific for PetCBF2 gene were generated by PCR amplification of 3'UTR region using CBF2ProbeF [SEQ ID NO: 19] and CBF2ProbeR [SEQ ID NO: 20]. Probes specific for PetCBF3 gene were generated by PCR amplification of 3'UTR region using CBF3ProbeF [SEQ ID NO: 21] and CBF3ProbeR [SEQ ID NO: 22]. The actin gene of *Petunia* was used as RNA loading control. The probe for Actin was obtained from *Petunia* by PCR using ActinF [SEQ ID NO: 25] and ActinR [SEQ ID NO: 26] as primers.

Total RNA was isolated from leaf tissue of control and treated plants by using TRIZOL reagent (Invitrogen, Carlsbad, Calif.). Fifteen microgram total RNA per sample was loaded on 1% agarose-formaldehyde gels. Transfer of the separated total RNA onto HYBOND-XL membranes (Amersham Biosciences, Piscataway, N.J.), and hybridization with radiolabeled probes was carried out following standard procedures (Sambrook et al. 1989). FIG. 1 illustrates the result of PetCBF1-3 gene expression analysis as described above.

Example 2

Transcription Factor PetCBF4 which is Induced by Cold, Drought, and Salinity Stress in Plants Isolation of PetCBF4

The procedure for obtaining clones as outlined in Example 1 was followed. One clone was obtained using ParF2 [SEQ ID NO: 10] and ParR4 [SEQ ID NO: 16] was named as PetCBF4 [SEQ ID NO: 30]. The sequences of the primers used are given in Table 2.

Analysis of PetCBF4 Gene Expression

In Northern hybridization, total RNA is isolated, run on gels, transferred onto nylon membranes and probed with fragments specific to a particular gene so that its expression can be monitored.

Cold treatment: *Petunia hybrida* v26 seeds were sown in the pots and grown at 22° C. in the green house. Four-week-old plants were subjected to cold treatment by placing them in a growth chamber set at 4° C. for 2 h.

Drought treatment: *Petunia hybrida* v26 seeds were sown in the pots and grown at 22° C. in the green house. Leaves from four-week-old plants were subjected to drought by detaching them from the plant and leaving at room temperature for 2 h.

Salinity treatment: *Petunia hybrida* v26 plants were hydroponically grown in nutrient solution. Four-week-old plants were subjected to salinity treatment by supplementing the nutrient solution with 250 mM sodium chloride.

Control: Four-week-old plants maintained at 22 C.

Northern hybridization: Probes specific for PetCBF4 gene [SEQ ID NO: 30] were generated by PCR amplification of the 3'UTR region using CBF4ProbeF [SEQ ID NO: 23] and CBF4ProbeR [SEQ ID NO: 24]. the actin gene of *Petunia* was used as RNA loading control. The probe for Actin was obtained from *Petunia* by PCR using ActinF [SEQ ID NO: 25] and ActinR [SEQ ID NO: 26] as primers.

Total RNA was isolated from leaf tissue of control and treated plants by using TRIZOL reagent (Invitrogen, Carlsbad, Calif.). Fifteen microgram total RNA per sample was loaded on 1% agarose-formaldehyde gels. Transfer of the separated total RNA onto Hybond-XL membranes (Amersham Biosciences, Piscataway, N.J.), and hybridization of radiolabeled probe were carried out following standard procedures (Sambrook et al 1989).

FIG. 2 illustrates PetCBF4 gene expression as described above.

Table 2—Primer used for isolation of CBF genes and for generation of probes for Northern hybridization

| Primer | SEQ ID NO: | Sequence |
|---|---|---|
| PetF4 | 1 | AATCCNAARAARCCNGCNG |
| PetR5 | 2 | ATCAGCRAARTTNARRCANGC |
| 3RACE1 | 3 | GGGAGGAAGAAGTTTCAAGAAACTCGACATCC |
| 3RACE2 | 4 | GGGAGGAAGAAGTTTCAAGAAACACGACATCC |
| 3RACE3 | 5 | GCCGGGAGGAAGAAGTTTAGAGAAACACGACA |
| 5RACE1 | 6 | GGATGTCGAGTTTCTTGAAACTTCTTCCTCCC |
| 5RACE2 | 7 | GGATGTCGTGTTTCTTGAAACTTCTTCCTCCC |
| 5RACE3 | 8 | TGTCGTGTTTCTCTAAACTTCTTCCTCCCGGC |
| ParF1 | 9 | CCTCAAACTGAAATAACATTCAGTACTAGTACT |
| ParF3 | 10 | CCTCTAACTGAAACAACATCCAATACAACC |
| ParF2 | 11 | TAACATTCAGTACTAGTACTATACACTTACTA |
| ParF4 | 12 | CAAAAACCTCAAACTGAACAACATTC |
| ParR1 | 13 | GGCAAACTACACGATGTTCTTGTCTCTCATC |
| ParR2 | 14 | TGGATCTTTCATTCAATACAAGGGCTTGG |

-continued

| Primer | SEQ ID NO: | Sequence |
|---|---|---|
| ParR3 | 15 | CAGTCAAATGTCGTGGTTTGAAAAAACCG |
| ParR4 | 16 | CCGCGCCAAGTCAAACACAGACACTC |
| CBF1ProbeF | 17 | CAAGAAGTCACTCCGGCTTT |
| CBF1ProbeR | 18 | TTGCATTCAAAAGTGGCAAA |
| CBF2ProbeF | 19 | AATTCTGTTAGTACTTCTTTGGGATAG |
| CBF2ProbeR | 20 | TTAGCTGCTCACTTGGATCTTTC |
| CBF3ProbeF | 21 | TTGGTACCTAATATTTGGACGGTA |
| CBF3ProbeR | 22 | TCAAATGTCGTGGTTTGAAAAA |
| CBF4ProbeF | 23 | ATATTTGGGCGGTACGTCTG |
| CBF4ProbeR | 24 | AGATTTGTTTTGGACCACATGA |
| ActinF | 25 | GAAGCGCCTCTGAACCCAAA |
| ActinR | 26 | CCGCAGCTTCCATTCCAATC |
| PetCBF1 | 27 | See the Sequence Listing |
| PetCBF2 | 28 | See the Sequence Listing |
| PetCBF3 | 29 | See the Sequence Listing |
| PetCBF4 | 30 | See the Sequence Listing |

Example 3

*Agrobacterium tumefaciens*-Mediated Transformation of Cereal Shoot Meristems

PetCBF1 [SEQ ID NO: 27], PetCBF2 [SEQ ID NO: 28], PetCBF3 [SEQ ID NO: 29], or PetCBF4 [SEQ ID NO: 30] sequences may be inserted into pDONR201 (Invitrogen), pBI121, pBIN20, pEarleyGate100 (ABRC), pEarleyGate102 (ABRC) or pCAMBIA. PetCBF3 [SEQ ID NO: 29] was inserted in pCAMBIA using methods routine in the art to create pC1300. pC1300 was introduced into *Agrobacterium tumefaciens* LBA 4404 using methods routine in the art.

Three different strains of *Agrobacterium tumefaciens* (LBA 4404, GV3101, and EHA 105) were grown overnight on LB medium supplemented with kanamycin and gentamycin (50 mg/L each) with shaking (200×g) at 26-28° C. One sample included the *Agrobacterium tumefaciens* LBA 4404 that previously received pC1300. The bacterial optical density (OD) was read on a Beckman spectrophotometer (Beckman Coulter, Fullerton, Calif.) at 660 nm. One hour before the *A. tumefaciens* reached the desired OD of 1-1.5, 200 µM acetosyringone was added. Following this, the cells were centrifuged at 2000×g for 10 min at room temperature. After discarding the supernatant, the pellet was resuspended in resuspension medium (half-strength MS salts (Murashige and Skoog (1962) Physiol. Plant 15(3): 473-497, which is hereby incorporated by reference as if fully set forth)+1% w/v glucose+200 µM acetosyringone (pH 5.2)). Cell density was readjusted to an OD of 0.8 at 660 nm by diluting with resuspension medium.

Maize shoot meristems were incubated in the *A. tumefaciens* cell suspensions for 3 h, plated on cocultivation medium (half-strength MS salts+2% w/v glucose), and incubated in the dark for 3 to 4 days. Meristems were transferred to auxin-supplemented callus-induction media containing carbenicillin (500 mg/L) and cefotaxime (250 mg/L). The cultures were reincubated in the dark and regularly subcultured every 15 days. Alternatively, the infected shoot meristems were grown on a modified MS medium containing 6-benzylaminopurine (BAP; 5-10 mg/L) and kinetin (Kn; 0.5-2.0 mg/L) and regenerated using organogenesis in the light.

Results using this protocol were reported in Sairam et al (2003) Genome 46(2):323-9 which is hereby incorporated by reference as if fully set forth. The rate of T-DNA transfer was high using any of the three *A. tumefaciens* strains. In all cases multiple cells of each shoot meristem infected expressed their respected selectable markers.

Example 4

Biolistic Mediated Transformation

Plasmid DNA containing: PetCBF1 [SEQ ID NO: 27], PetCBF2 [SEQ ID NO: 28], PetCBF3 [SEQ ID NO: 29], and PetCBF4 [SEQ ID NO: 30] was isolated using a HiSpeed Plasmid Midi Kit (Qiagen Sciences, Maryland, USA) and the DNA concentration was adjusted to 900 ng/µl. Gold particles of 0.6 µm in diameter (Bio-Rad Laboratories, Hercules, Calif., USA) were coated with 10 µl plasmid DNA. The coated gold particles were then mixed with 50 µl of 2.5 M $CaCl_2$, 20 µl of 0.1 M sperimidine and were vortexed for 20 minutes at 4° C. The coated particles were washed 3 times with 200 µl ethanol and centrifuged for 1 minute after each wash. Finally, the particles were re-suspended in 35 µl ethanol and kept on ice. 8-9 µl of the suspension were spread on each macro-carrier and allowed to dry prior to bombardment.

A total of twenty-nine experiments were carried out using approximately 3000 split-seed explants. The different parameters tested were as follows: helium pressure (1100, 1350 and 1550 psi), target distance (6 and 9 cm), and number of shots on explants (once or twice). These parameters have proven useful for the successful identification of maize transgenics using the split seed explant.

Example 5

Regeneration and Maize Genotypes

Six different hybrids and an inbred of corn were tested for suitability with *Agrobacterium* mediated transformation. The hybrids LH 74×A 641, LH 262×LH 252, LH 198×LH 227, FR 1064×FR 1064 (SDMS)×LH 185, and LH 176×LH 177 DMS were obtained from the Indiana Crop Improvement Association (Lafayette, Ind.) and the inbred line R23 ('CHAMPAIGN WHITE PEARL') was obtained from Pioneer Hi-Bred (Johnston, Iowa). Six of these proved regenerable using somatic embryogenesis and the seventh using organogenesis. This regeneration protocol was also utilized with the *Tripsacum* variety "PETE", with multiple maize genotypes, with wheat, and with sorghum. All genotypes were transformed with PetCBF3 [SEQ ID NO: 29] using *Agrobacterium* that had received pC1300. None of the lines tested for regeneration capacity proved refractory and thus there exists a capacity to transform myriad types of plants with PetCBF nucleic acids.

Example 6

Somatic Embryogenesis

Meristem-derived callus was produced from the products of example 5, including PetCBF [SEQ ID NO: 29] containing samples. Prolonged incubation of the meristem-derived callus on modified MS medium supplemented with 2,4-dichlorophenoxyacetic acid (2,4-D) resulted in proliferation of somatic embryos. Calli containing numerous somatic embryos were transferred to MS regeneration medium supplemented with myoinositol and glycine (100 mg/L), to form green plantlets that were then transferred to soil and acclimatized in standard greenhouse conditions.

Example 7

Direct Organogenesis, Coupling High Frequency T-DNA Transfer and Robust Regeneration Shoot meristems isolated from Zea mays seeds germinated on modified MS medium containing auxin were cocultivated with A. tumefaciens containing test DNA for 3 days in the absence of light. One sample of A. tumefaciens previously received DNA comprising PetCBF3 [SEQ ID NO: 29]. After 3 days, the meristem cultures were transferred to a modified MS medium containing two cytokinins (0.5 mg Kn/L+5-10 mg BA/L) in addition to carbenicillin and cefotaxime (50-500 mg/L) and incubated in the light.

Example 8

Plant Regeneration from Soybean Cotyledonary Nodal Embryogenic Callus induced on an Auxin Medium In addition to monocots, dicots could also be transformed with the PetCBF1 [SEQ ID NO: 27], PetCBF2 [SEQ ID NO: 28], PetCBF3 [SEQ ID NO: 29], or PetCBF4 [SEQ ID NO: 30] and other sequences disclosed herein to increase their stress tolerance and resistance. To illustrate, mature soybean seeds were surface sterilized with 0.1% $HgCl_2$ for 10 minutes followed by five washes with sterile water and germinated on a modified MS based auxin medium containing 2 mg/l 2,4-D from about 24 hours to about 96 hours. The next step was separating the two cotyledons from the hypocotyls and epicotyl regions. The cotyledon explants were collected 3-5 days post germination and incubated on a high auxin-containing medium (5-10 mg/l 2,4-D) for inducing callus at the cotyledonary nodes. Callus initiation was seen in 3-5 days. At this stage the cotyledonary explants with embryogenic callus at the nodal region were treated with Agrobacterium containing test DNA containing the gene for GFP (Green Fluorescent Protein) using the procedures described above. Alternatively, the cotyledon explants can be directly incubated in Agrobacterium solution for direct organogenesis of plants. After 3 days co-cultivation the cotyledonary nodal callus explants were placed on an incubating medium comprising high cytokinin (2-20 mg/l BAP) modified MS medium supplemented with amino acids glutamine (50 mg/l), asparagines (5-10 mg/l), cysteine (500 mg/l). The explants were incubated in light to regenerate plants.

The explants were viewed under Olympus SZX12 epifluorescence GFP (Green Fluorescent Protein) stereomicroscope equipped with an Olympus filter cube containing 460-490 nm excitation filters and emission filter 510 interference. The green and uniform expression seen on the cotyledons indicated the high rate of gene delivery for GFP. GFP could be linked to a PetCBF gene or any of the sequences disclosed herein. Shoot regeneration started from day 5 after incubation on the medium. The number of multiple shoots per each explant was 4-5. The frequency of callus indication was about 60 to at least about 80% and the plant regeneration frequency ranged from 40 to about 60%.

Example 9

Selection of Transformants

Following transformation transgenic plants can be selected from non-transgenic plants using standard PCR. The use of selectable and/or screenable markers may not be necessary because the rate of T-DNA transfer is high and multiple independent shoots can be obtained per explant. The PetCBF genes PetCBF1 [SEQ ID NO: 27], PetCBF2 [SEQ ID NO: 28], and PetCBF3 [SEQ ID NO: 29] could subsequently be used as selectable markers following cold challenge. Transgenic plants could also be selected using drought challenge when transformed with either PetCBF3 [SEQ ID NO: 29] or PetCBF4 [SEQ ID NO: 30]. Transgenic plants could further be selected when transformed with PetCBF4 [SEQ ID NO: 30] and challenging, either alone or in any combination, with any of the following: cold temperatures (below 20° C.), drought (deprivation of water for more than 13 days), and salinity (growth in 250 mM NaCl).

Example 10

Identification of Transgenic Drought Resistant Plants

Petunia and maize plants were tested for drought resistance. Control plants were non-transgenic, and test plants were transgenic for PetCBF3 [SEQ ID NO: 29]. Fully-grown plants just before flowering were used for drought tolerance experiments. On day one, all the plants were watered to saturation, and then they were not watered for 9 days. Starting on the 10th day, 5 non-transgenic plants and one set of 12 transgenic plants were watered everyday. The number of plants that became fully turgid was counted 24 h after watering. Recovery from chlorophyll damage due to drought stress was visually evaluated from the change in the color of the leaves from yellowish green or yellow to green after watering. The number of plants that completely recovered from chlorophyll damage was counted 10 days after watering.

All the plants remained fully turgid for six days after watering was withheld. Plants showed wilting starting on the 7th day and wilting progressed from mature leaves to young leaves. At up to 13 days of drought stress, both non-transgenic and transgenic plants recovered completely after irrigation. Transgenic plant tolerated beyond 13 days of water stress and up to 15 days.

Example 11

Identification of Transgenic Cold/Freeze Resistant Plants

Petunia plants containing PetCBF4 [SEQ ID NO: 30] were tested at different low temperatures for different durations. Control plants were frozen in 2 h at −6° C. and collapsed when brought to room temperature. Petunia containing PetCBF4 [SEQ ID NO: 30] could survive up to 13 h at −6° C.

Example 12

Identification of Transgenic Saline Resistant Plants

Petunia plants containing PetCBF4 [SEQ ID NO: 30] were grown in pots. Control and treated plants were irrigated with 250 mM NaCl. Observations were made for 4 weeks. The control plants completely withered but the petunia plants containing PetCBF4 [SEQ ID NO: 30] remained green and healthy.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. An isolated nucleic acid comprising a nucleotide sequence encoding a DREB1/CBF protein having at least 90% amino acid sequence identity to SEQ ID NO: 32, and wherein expression of said protein in a plant results in increased tolerance to dehydration stress in said plant.

2. The nucleic acid of claim 1, wherein said nucleotide sequence is operatively linked to a promoter.

3. The nucleic acid of claim 2 incorporated in a plant host.

4. The nucleic acid of claim 3 wherein the host is selected from the group consisting of a plant, plant tissue and a plant cell.

5. The nucleic acid of claim 3, wherein the host is a monocotyledonous plant.

6. The nucleic acid of claim 3, wherein the host is a dicotyledonous plant.

7. The nucleic acid of claim 3 wherein the host is selected from the group consisting of petunia, soybean, wheat, corn, switchgrass, miscanthus, willow, poplar, potato, cotton, rice, oilseed rape, sunflower, alfalfa, clover, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, mint, labiates, rosaceous fruits, and vegetable brassicas.

8. The nucleic acid of claim 1, wherein the nucleotide sequence encoding said protein has the amino acid sequence as set forth in SEQ ID NO: 32.

9. A vector comprising the nucleic acid of claim 1.

10. The vector of claim 9 wherein the vector is an expression vector comprising regulatory elements operatively linked to said nucleic acid.

11. The vector of claim 9 further comprising a promoter operatively linked to said nucleic acid.

12. The vector of claim 11 wherein the promoter is selected from the group consisting of a tissue specific promoter and an inducible promoter.

13. The vector of claim 11 wherein the promoter is a flower, fruit or seed specific promoter.

14. The vector of claim 11, wherein the promoter regulates transcription at a temperature equal to or less than about 20° C.

15. The vector of claim 9, where the vector is capable of being transformed into a plant host.

16. The vector of claim 15, wherein the host is a monocotyledonous plant.

17. The vector of claim 15, wherein the host is a dicotyledonous plant.

18. The vector of claim 15 wherein the host is selected from the group consisting of petunia, soybean, wheat, corn, switchgrass, miscanthus, willow, poplar, potato, cotton, rice, oilseed rape, sunflower, alfalfa, clover, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, mint, labiates, rosaceous fruits, and vegetable brassicas.

19. A transgenic plant transformed with a nucleic acid comprising a nucleotide sequence encoding a DREB 1/CBF protein having at least 90% amino acid sequence identity to SEQ ID NO: 32, wherein said nucleotide sequence is operably linked to a promoter, and wherein expression of said protein in a plant results in increased tolerance to dehydration stress in said transformed plant as compared to an untransformed plant of the same species lacking said nucleic acid.

20. The transgenic plant of claim 19, wherein the nucleotide sequence encoding said protein has the amino acid sequence as set forth in SEQ ID NO: 32.

21. The transgenic plant of claim 19 wherein the plant is a monocotyledon.

22. The transgenic plant of claim 19 wherein the plant is a dicotyledon.

23. The transgenic plant of claim 19 wherein the plant is selected from the group consisting of petunia, soybean; wheat, corn, switchgrass, miscanthus, willow, poplar, potato, cotton, rice, oilseed rape, sunflower, alfalfa, clover, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, spinach, squash, sweet corn, tobacco, tomato, watermelon, mint, labiates, rosaceous fruits, and vegetable brassicas.

24. A method of producing a plant having increased tolerance to a dehydration stress comprising the steps of:
  (a) transforming plant cells with an expression vector which comprises a nucleic acid comprising a nucleotide sequence encoding a DREB 1/CBF protein having at least 90% amino acid sequence identity to SEQ ID NO: 32, wherein said nucleotide sequence is operably linked to a promoter;
  (b) expressing said protein in the transformed plant cells;
  (c) regenerating transgenic plants from said transformed plant cells; and
  (d) identifying a transgenic plant from said transgenic plants of step (c) which exhibits increased tolerance to said dehydration stress as compared to a plant that is not transformed with said expression vector.

25. The method of claim 24, wherein said protein has the amino acid sequence as set forth in SEQ ID NO: 32.

26. The method of claim 24, wherein said plant is a monocotyledon.

27. The method of claim 24, wherein said plant is a dicotyledon.

28. The method of claim 24, wherein said plant is selected from the group of plants consisting of petunia, soybean, wheat, corn, switchgrass, miscanthus, willow, poplar, potato, cotton, rice, oilseed rape, sunflower, alfalfa, clover, sugarcane, turf, banana, blackberry, blueberry, strawberry, raspberry, cantaloupe, carrot, cauliflower, coffee, cucumber, eggplant, grapes, honeydew, lettuce, mango, melon, onion, papaya, peas, peppers, pineapple, pumpkin, squash, sweet corn, tobacco, tomato, watermelon, mint and other labiates, rosaceous fruits, and vegetable brassicas.

* * * * *

UNITED STATES PATENT AND TRADEMARK OFFICE
CERTIFICATE OF CORRECTION

| | | |
|---|---|---|
| PATENT NO. | : 8,173,869 B2 | Page 1 of 1 |
| APPLICATION NO. | : 12/090908 | |
| DATED | : May 8, 2012 | |
| INVENTOR(S) | : Goldman et al. | |

It is certified that error appears in the above-identified patent and that said Letters Patent is hereby corrected as shown below:

Col. 64, Claim 28, Line 14:
ADD after pumpkin, --spinach--

Signed and Sealed this
Seventeenth Day of July, 2012

David J. Kappos
*Director of the United States Patent and Trademark Office*

SEQUENCE LISTING

<160> NUMBER OF SEQ ID NOS: 61

<210> SEQ ID NO 1
<211> LENGTH: 19
<212> TYPE: DNA
<213> ORGANISM: Artificial
<220> FEATURE:
<223> OTHER INFORMATION: Degenerate PCR Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 1
aatccnaara arccngcng                                                  19

<210> SEQ ID NO 2
<211> LENGTH: 21
<212> TYPE: DNA
<213> ORGANISM: Artificial
<220> FEATURE:
<223> OTHER INFORMATION: Degenerate PCR Primer
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 2
atcagcraar ttnarrcang c                                               21

<210> SEQ ID NO 3
<211> LENGTH: 32
<212> TYPE: DNA
<213> ORGANISM: Petunia x hybrida v26

<400> SEQUENCE: 3
gggaggaaga agtttcaaga aactcgacat cc                                   32

<210> SEQ ID NO 4
<211> LENGTH: 32
<212> TYPE: DNA
<213> ORGANISM: Petunia x hybrida v26

<400> SEQUENCE: 4
gggaggaaga agtttcaaga aacacgacat cc                                   32

<210> SEQ ID NO 5
<211> LENGTH: 32
<212> TYPE: DNA
<213> ORGANISM: Petunia x hybrida v26

<400> SEQUENCE: 5
gccgggagga agaagtttag agaaacacga ca                                   32

<210> SEQ ID NO 6

```
<211> LENGTH: 32
<212> TYPE: DNA
<213> ORGANISM: Petunia x hybrida v26

<400> SEQUENCE: 6
ggatgtcgag tttcttgaaa cttcttcctc cc                              32

<210> SEQ ID NO 7
<211> LENGTH: 32
<212> TYPE: DNA
<213> ORGANISM: Petunia x hybrida

<400> SEQUENCE: 7
ggatgtcgtg tttcttgaaa cttcttcctc cc                              32

<210> SEQ ID NO 8
<211> LENGTH: 32
<212> TYPE: DNA
<213> ORGANISM: Petunia x hybrida v26

<400> SEQUENCE: 8
tgtcgtgttt ctctaaactt cttcctcccg gc                              32

<210> SEQ ID NO 9
<211> LENGTH: 33
<212> TYPE: DNA
<213> ORGANISM: Petunia x hybrida v26

<400> SEQUENCE: 9
cctcaaactg aaataacatt cagtactagt act                             33

<210> SEQ ID NO 10
<211> LENGTH: 30
<212> TYPE: DNA
<213> ORGANISM: Petunia x hybrida v26

<400> SEQUENCE: 10
cctctaactg aaacaacatc caatacaacc                                 30

<210> SEQ ID NO 11
<211> LENGTH: 32
<212> TYPE: DNA
<213> ORGANISM: Petunia x hybrida v26

<400> SEQUENCE: 11
taacattcag tactagtact atacacttac ta                              32

<210> SEQ ID NO 12
<211> LENGTH: 26
<212> TYPE: DNA
<213> ORGANISM: Petunia x hybrida v26

<400> SEQUENCE: 12
caaaaacctc aaactgaaca acattc                                     26

<210> SEQ ID NO 13
<211> LENGTH: 31
<212> TYPE: DNA
<213> ORGANISM: Petunia x hybrida v26

<400> SEQUENCE: 13
ggcaaactac acgatgttct tgtctctcat c                               31

<210> SEQ ID NO 14
```

```
<211> LENGTH: 29
<212> TYPE: DNA
<213> ORGANISM: Petunia x hybrida v26

<400> SEQUENCE: 14
tggatctttc attcaataca agggcttgg                                              29

<210> SEQ ID NO 15
<211> LENGTH: 29
<212> TYPE: DNA
<213> ORGANISM: Petunia x hybrida v26

<400> SEQUENCE: 15
cagtcaaatg tcgtggtttg aaaaaaccg                                              29

<210> SEQ ID NO 16
<211> LENGTH: 26
<212> TYPE: DNA
<213> ORGANISM: Petunia x hybrida v26

<400> SEQUENCE: 16
ccgcgccaag tcaaacacag acactc                                                 26

<210> SEQ ID NO 17
<211> LENGTH: 20
<212> TYPE: DNA
<213> ORGANISM: Petunia x hybrida v26

<400> SEQUENCE: 17
caagaagtca ctccggcttt                                                        20

<210> SEQ ID NO 18
<211> LENGTH: 20
<212> TYPE: DNA
<213> ORGANISM: Petunia x hybrida v26

<400> SEQUENCE: 18
ttgcattcaa aagtggcaaa                                                        20

<210> SEQ ID NO 19
<211> LENGTH: 27
<212> TYPE: DNA
<213> ORGANISM: Petunia x hybrida v26

<400> SEQUENCE: 19
aattctgtta gtacttcttt gggatag                                                27

<210> SEQ ID NO 20
<211> LENGTH: 23
<212> TYPE: DNA
<213> ORGANISM: Petunia x hybrida v26

<400> SEQUENCE: 20
ttagctgctc acttggatct ttc                                                    23

<210> SEQ ID NO 21
<211> LENGTH: 24
<212> TYPE: DNA
<213> ORGANISM: Petunia x hybrida v26

<400> SEQUENCE: 21
ttggtaccta atatttggac ggta                                                   24

<210> SEQ ID NO 22
```

```
<211> LENGTH: 22
<212> TYPE: DNA
<213> ORGANISM: Petunia x hybrida v26

<400> SEQUENCE: 22
tcaaatgtcg tggtttgaaa aa                                                  22

<210> SEQ ID NO 23
<211> LENGTH: 20
<212> TYPE: DNA
<213> ORGANISM: Petunia x hybrida v26

<400> SEQUENCE: 23
atatttgggc ggtacgtctg                                                     20

<210> SEQ ID NO 24
<211> LENGTH: 22
<212> TYPE: DNA
<213> ORGANISM: Petunia x hybrida v26

<400> SEQUENCE: 24
agatttgttt tggaccacat ga                                                  22

<210> SEQ ID NO 25
<211> LENGTH: 20
<212> TYPE: DNA
<213> ORGANISM: Petunia

<400> SEQUENCE: 25
gaagcgcctc tgaacccaaa                                                     20

<210> SEQ ID NO 26
<211> LENGTH: 20
<212> TYPE: DNA
<213> ORGANISM: Petunia x hybrida v26

<400> SEQUENCE: 26
ccgcagcttc cattccaatc                                                     20

<210> SEQ ID NO 27
<211> LENGTH: 1219
<212> TYPE: DNA
<213> ORGANISM: petunia x hybrida v26

<400> SEQUENCE: 27
aagcagtggc atcaacgcag agtacgcggg gaaaaaacaa aaacctctaa ctgaaacaac         60
atccaataca accatacttt ttctactctc aatatatcag tgatcaagaa atggatatct        120
ttggaagcta ttattcagac acacttcctg cagcatcagc tcctactttt tggcctttag        180
acgtgcctga atattcttca ccaatatctg ataatagcag ctgcagtaat aatagagcta        240
atcattctga tgaagaggtg atgttagctt caaataaccc gaaaaagcga gccgggagga        300
agaagtttag agaaacacga catccagtat acaggggagt caggaagagg aattcaggca        360
agtgggtttg tgaagtgaga gaacccaata agcaatcaag aatttggctt ggaacattcc        420
caactgctga atggcggct agagctcatg acgtggcggc tattgcattt aggggtcgtt        480
ctgcttgttt gaattttgcg gactctgctt ggaagttgcc taccctgct tcttccgacc        540 ccaaggatat tcagaaggcg gccgcagagg ccgccgaggc ttttaggcct ttggagtcag        600
aaggggtaca ttcagctgga gaagaatcaa agaagagag caccactcca gaaacagcag        660
agagtatgta ctttatggat gaagaggcac ttttctgcat gcctggatta cttgcaaata        720
```

-continued

```
tggctgaagg gctaatgtta cctccacctc aatgttcaga agttggagat cattttatgg      780
aagctgatgc tgacatgcct ttatggagtt attctgtcta attcttctag ttattactct      840
ttttaacata atggagtata atttagtaca gtttcttaaa ttaggattta ggagacatta      900
gtagttttgt acctaatatt tggatggtac agtgtacctt ttagtaacga tgcaaatagt      960
actactactc tgttctgcta gtatcaagaa gtcactccgg ctttgtgcaa atcattggcc     1020
tagacttcta agactatttt agcggcagtg aacataagt gagataatag tactactaat      1080
tagtattagt aatattgatg agagacaaga acatcgtgta gtttgccact tttgaatgca     1140
atattttaag tagaggcatt aggtgtaaca gccttctcaa tgataatcac agttgagtca     1200
aaaaaaaaaa aaaaaaaaa                                                 1219
```

<210> SEQ ID NO 28
<211> LENGTH: 1159
<212> TYPE: DNA
<213> ORGANISM: Petunia x hybrida v26

<400> SEQUENCE: 28

```
ctaatacgac tcactatagg gcaagcagtg gtatcaacgc agagtacgcg gggaaaacaa       60
aaacctcaaa ctgaacaaca ttcaatatta gtgaaacact ttttactctc tcaaaatgga      120
tatctttgga agctattatt cagacatact tcctatagaa ttgcctgaat attcttcacc      180
aatgtctgac aatagcagct gcagcaatta tagagctaat cattcagatg acgaagtgat      240
gttagcttca ataaccccca agaagtgtgc tgggaggaag aagttagag aaacacgaca      300 tccagtatac aggggagtca ggaagaggaa cggcaagtgg gtttgtgaag tcagagagcc      360
caataagaaa tcaagaattt ggcttggttc atttccaact gctgaaatgg ccgctagagc      420
tcacgatgta gcggctattg cattaagggg tcgttctgct tgcttgaact ttgctgactc      480
tgcttggaag ttgcctatcc ctgcttcctc aaccccaag gatattcaga aggcggccgc      540
agaggccgcc aaggctttca gggagtcggg agaagaatca aaggaagaga gcagtactcg      600
tgaaacgcca gaaagatgt tctttatgga tgaagaggca cttttctgca tgccagaatt      660
acttgcaaat atggctgaag gactaatgtt acctccacca tctcaatgtt cagatgttgg      720
agagcatttt atggatgctg atgttgacat gcctttatgg agttattcta tctaaattag      780
taattctgtt agtacttctt tgggatagtc tatgatcttc tctataagca aagtcaagat      840
gcaagcagaa tgcttcaagt gaagttcctt aaaagtagga tttaggcgat ataggactat      900
tggtagcttc gtactcaata tttggatggt acgtctgtac ataggtgagg taaatatggt      960
aagatctagg tattcttatg tttgcaccgg aaagtggttt cggctaaatg caaatcattg     1020
acactgcgga caagaatatt atagcgtcac caattcgtga agacttgtga attggtggct     1080
tggttatttc caagcccttg tattgaatga agatccaag tgagcagcta atttgggagc      1140
aaaaaaaaaa aaaaaaaaa                                                 1159
```

<210> SEQ ID NO 29
<211> LENGTH: 1024
<212> TYPE: DNA
<213> ORGANISM: Petunia x hybrida v26

<400> SEQUENCE: 29

```
gaagaaacaa aaacctcaaa ctgaaataac attcagtact agtactatac acttttaca       60 caaaatatca gtgatcaaga aatggatatt tttgcaagat attattcgga ccaacttcct      120
atagcatcag ctgctacttt ttggcctta gaagtggctg aatattcttc accaatgtct      180
```

-continued

```
gatattagta ataatagagc taatctttca gatgaagaag tgatgttagc ttcaaataac        240
ccaaagaagc gagctgggag gaagaagttt caagaaacac gacatccagt atacagggga        300
gtgaggaaga ggagttcagg caagtgggtt tgtgaagtga gagagcccaa taagaaatca        360
agaatttggc taggcacata taaactgctg aaatggcagc tagagctca tgacgtcgca         420 gctattgcat taaggggtcg ttctgcttgt ctgaactttg ctgactctgc ttggaagttg        480
catatcccgg cttcctccaa agccaaggat attcagaagg cggccacaga ggctgcctcg        540
gctttccagg aatcaaagga agagggcact actcctgaaa cgccagaaaa gatgctcttt        600
atggatgaag aggcactttt ctacatgcct ggattacttg caaatatggc tgaaggacta        660
atgttacctc taccacctca atgttcagaa gttggagatc attttatgga agctgctgct        720
gacatgcctt tgtggagtta ttcttctaa ttgttttagt ccagtttctt aaattaggat         780
ttaggagacg ttagtagttt ggtacctaat atttggacgg tacagtgtat acaatttagt        840
aacgatgtta gatagtacta ctactctgtt ctgctagaat caagaagttc ttctggttta        900
atgcagaaca gaggatgttt gttatagcgt aattggatta ttttgtttag gcaagtgaat        960
aagaaaattt cttcggtttt ttcaaaccac gacatttgac aaaaaaaaa aaaaaaaaa        1020 aaaa                                                                    1024
```

<210> SEQ ID NO 30
<211> LENGTH: 1020
<212> TYPE: DNA
<213> ORGANISM: Petunia x hybrida v26

<400> SEQUENCE: 30

```
gaaaataaaa acaaaaacct caaactgaaa taacattcag tactagtact atacacttac         60
tattactctc aaaatatgag tgatcaagaa atggatattt ttggacgata ttattctgac        120
caacttccta tagcatcagc tgctacattt tggcctttag aagtggctga atattctgat        180
aatagcagca gcagcagtaa taatagagct aatgtttcag atgaagaagt gatgttagct        240
tcaaataacc caaagaagcg agctgggagg aagaagtttc aagaaactcg acatccagta        300
tataggggag tgaggaagag gaattcaggg aagtgggttt gtgaagtgag agagcccaat        360
aagaaatcaa gaatatggct tggaacatat tcaactgcag aaatggcagc tagagctcat        420
gatgttgcgg ctattgcatt aaggggtcgt gctgcttgtc taaactttgc tgactctgct        480
tggaagttac ctatcccggc ttcctccaaa gccaaggata tccagaaggc ggccacagag        540
gccgccgcca cggcttttct ggaaccagga gagcctgaaa ctcgaaaaaa aaatatgttg        600
tttatggatg aagaggcact ttttttgcatg cctggattac ttgcaaatat ggctgaagga        660
ctaatgttaa ctccacctca atgttatgga aacattttta tggaagctga tgctgaagtg        720
cctttatgga gttattagat ctccataatt agacattcta tgatcttcat acacaatatt        780
tgggcggtac gtctgtacat gagtgagata gtaatccgcc agtcccaaaa tgagtgtctg        840
tgtttgactt ggcgcggaga ttaagataac agagaagact tttgaatcat gttgttgtgt        900
gtaatatggg ccacttattt ttaaatcatg tggtccaaaa caaatcttga aattaaagag        960
ttataaaata tggaaagaat cactctttttt agacaaaaaa aaaaaaaaaa aaaaaaaaa        1020
```

<210> SEQ ID NO 31
<211> LENGTH: 18
<212> TYPE: DNA
<213> ORGANISM: Artificial
<220> FEATURE:
<223> OTHER INFORMATION: PCR Primer

```
<400> SEQUENCE: 31
tttttttttt tttttttt                                                 18

<210> SEQ ID NO 32
<211> LENGTH: 236
<212> TYPE: PRT
<213> ORGANISM: petunia x hybrida v26

<400> SEQUENCE: 32
```

Met Asp Ile Phe Gly Ser Tyr Tyr Ser Asp Thr Leu Pro Ala Ala Ser
1               5                   10                  15

Ala Pro Thr Phe Trp Pro Leu Asp Val Pro Glu Tyr Ser Ser Pro Ile
            20                  25                  30

Ser Asp Asn Ser Ser Cys Ser Asn Asn Arg Ala Asn His Ser Asp Glu
        35                  40                  45

Glu Val Met Leu Ala Ser Asn Asn Pro Lys Lys Arg Ala Gly Arg Lys
50                  55                  60

Lys Phe Arg Glu Thr Arg His Pro Val Tyr Arg Gly Val Arg Lys Arg
65                  70                  75                  80

Asn Ser Gly Lys Trp Val Cys Glu Val Arg Glu Pro Asn Lys Gln Ser
                85                  90                  95

Arg Ile Trp Leu Gly Thr Phe Pro Thr Ala Glu Met Ala Ala Arg Ala
            100                 105                 110

His Asp Val Ala Ala Ile Ala Phe Arg Gly Arg Ser Ala Cys Leu Asn
        115                 120                 125

Phe Ala Asp Ser Ala Trp Lys Leu Pro Thr Pro Ala Ser Ser Asp Pro
130                 135                 140

Lys Asp Ile Gln Lys Ala Ala Glu Ala Ala Glu Ala Phe Arg Pro
145                 150                 155                 160

Leu Glu Ser Glu Gly Val His Ser Ala Gly Glu Ser Lys Glu Glu
            165                 170                 175

Ser Thr Thr Pro Glu Thr Ala Glu Ser Met Tyr Phe Met Asp Glu Glu
            180                 185                 190

Ala Leu Phe Cys Met Pro Gly Leu Leu Ala Asn Met Ala Glu Gly Leu
            195                 200                 205

Met Leu Pro Pro Pro Gln Cys Ser Glu Val Gly Asp His Phe Met Glu
        210                 215                 220

Ala Asp Ala Asp Met Pro Leu Trp Ser Tyr Ser Val
225                 230                 235

```
<210> SEQ ID NO 33
<211> LENGTH: 219
<212> TYPE: PRT
<213> ORGANISM: Petunia x hybrida v26

<400> SEQUENCE: 33
```

Met Asp Ile Phe Gly Ser Tyr Tyr Ser Asp Ile Leu Pro Ile Glu Leu
1               5                   10                  15

Pro Glu Tyr Ser Ser Pro Met Ser Asp Asn Ser Ser Cys Ser Asn Tyr
            20                  25                  30

Arg Ala Asn His Ser Asp Asp Glu Val Met Leu Ala Ser Asn Asn Pro
        35                  40                  45

Lys Lys Cys Ala Gly Arg Lys Lys Phe Arg Glu Thr Arg His Pro Val
50                  55                  60

Tyr Arg Gly Val Arg Lys Arg Asn Gly Lys Trp Val Cys Glu Val Arg
65                  70                  75                  80

-continued

```
Glu Pro Asn Lys Lys Ser Arg Ile Trp Leu Gly Ser Phe Pro Thr Ala
                 85                  90                  95

Glu Met Ala Ala Arg Ala His Asp Val Ala Ile Ala Leu Arg Gly
            100                 105                 110

Arg Ser Ala Cys Leu Asn Phe Ala Asp Ser Ala Trp Lys Leu Pro Ile
            115                 120                 125

Pro Ala Ser Ser Asn Pro Lys Asp Ile Gln Lys Ala Ala Glu Ala
            130                 135                 140

Ala Lys Ala Phe Arg Glu Ser Gly Glu Glu Ser Lys Glu Glu Ser Ser
145                 150                 155                 160

Thr Arg Glu Thr Pro Glu Lys Met Phe Phe Met Asp Glu Glu Ala Leu
                165                 170                 175

Phe Cys Met Pro Glu Leu Leu Ala Asn Met Ala Glu Gly Leu Met Leu
            180                 185                 190

Pro Pro Pro Ser Gln Cys Ser Asp Val Gly Glu His Phe Met Asp Ala
            195                 200                 205

Asp Val Asp Met Pro Leu Trp Ser Tyr Ser Ile
            210                 215
```

<210> SEQ ID NO 34
<211> LENGTH: 222
<212> TYPE: PRT
<213> ORGANISM: Petunia x hybrida v26

<400> SEQUENCE: 34

```
Met Asp Ile Phe Ala Arg Tyr Tyr Ser Asp Gln Leu Pro Ile Ala Ser
1               5                   10                  15

Ala Ala Thr Phe Trp Pro Leu Glu Val Ala Glu Tyr Ser Ser Pro Met
            20                  25                  30

Ser Asp Ile Ser Asn Asn Arg Ala Asn Leu Ser Asp Glu Glu Val Met
            35                  40                  45

Leu Ala Ser Asn Asn Pro Lys Lys Arg Ala Gly Arg Lys Lys Phe Gln
        50                  55                  60

Glu Thr Arg His Pro Val Tyr Arg Gly Val Arg Lys Arg Ser Ser Gly
65                  70                  75                  80

Lys Trp Val Cys Glu Val Arg Glu Pro Asn Lys Lys Ser Arg Ile Trp
                85                  90                  95

Leu Gly Thr Tyr Ile Thr Ala Glu Met Ala Ala Arg Ala His Asp Val
            100                 105                 110

Ala Ala Ile Ala Leu Arg Gly Arg Ser Ala Cys Leu Asn Phe Ala Asp
            115                 120                 125

Ser Ala Trp Lys Leu His Ile Pro Ala Ser Ser Lys Ala Lys Asp Ile
        130                 135                 140

Gln Lys Ala Ala Thr Glu Ala Ala Ser Ala Phe Gln Glu Ser Lys Glu
145                 150                 155                 160

Glu Gly Thr Thr Pro Glu Thr Pro Glu Lys Met Leu Phe Met Asp Glu
                165                 170                 175

Glu Ala Leu Phe Tyr Met Pro Gly Leu Leu Ala Asn Met Ala Glu Gly
            180                 185                 190

Leu Met Leu Pro Leu Pro Pro Gln Cys Ser Glu Val Gly Asp His Phe
        195                 200                 205

Met Glu Ala Ala Ala Asp Met Pro Leu Trp Ser Tyr Ser Phe
    210                 215                 220
```

<210> SEQ ID NO 35
<211> LENGTH: 215

<212> TYPE: PRT
<213> ORGANISM: Petunia x hybrida v26

<400> SEQUENCE: 35

```
Met Asp Ile Phe Gly Arg Tyr Tyr Ser Asp Gln Leu Pro Ile Ala Ser
1               5                   10                  15
Ala Ala Thr Phe Trp Pro Leu Glu Val Ala Glu Tyr Ser Asp Asn Ser
            20                  25                  30
Ser Ser Ser Asn Asn Arg Ala Asn Val Ser Asp Glu Glu Val Met
        35                  40                  45
Leu Ala Ser Asn Asn Pro Lys Lys Arg Ala Gly Arg Lys Lys Phe Gln
    50                  55                  60
Glu Thr Arg His Pro Val Tyr Arg Gly Val Arg Lys Arg Asn Ser Gly
65                  70                  75                  80
Lys Trp Val Cys Glu Val Arg Glu Pro Asn Lys Lys Ser Arg Ile Trp
                85                  90                  95
Leu Gly Thr Tyr Ser Thr Ala Glu Met Ala Ala Arg Ala His Asp Val
            100                 105                 110
Ala Ala Ile Ala Leu Arg Gly Arg Ala Ala Cys Leu Asn Phe Ala Asp
        115                 120                 125
Ser Ala Trp Lys Leu Pro Ile Pro Ala Ser Ser Lys Ala Lys Asp Ile
    130                 135                 140
Gln Lys Ala Ala Thr Glu Ala Ala Thr Ala Phe Leu Glu Pro Gly
145                 150                 155                 160
Glu Pro Glu Thr Arg Lys Lys Asn Met Leu Phe Met Asp Glu Glu Ala
                165                 170                 175
Leu Phe Cys Met Pro Gly Leu Leu Ala Asn Met Ala Glu Gly Leu Met
            180                 185                 190
Leu Thr Pro Pro Gln Cys Tyr Gly Glu His Phe Met Glu Ala Asp Ala
        195                 200                 205
Glu Val Pro Leu Trp Ser Tyr
    210                 215
```

<210> SEQ ID NO 36
<211> LENGTH: 110
<212> TYPE: DNA
<213> ORGANISM: Petunia x hybrida v26

<400> SEQUENCE: 36

```
aagcagtggc atcaacgcag agtacgcggg gaaaaaacaa aaacctctaa ctgaaacaac    60
atccaataca accatacttt ttctactctc aatatatcag tgatcaagaa               110
```

<210> SEQ ID NO 37
<211> LENGTH: 115
<212> TYPE: DNA
<213> ORGANISM: Petunia x hybrida v26

<400> SEQUENCE: 37

```
ctaatacgac tcactatagg gcaagcagtg gtatcaacgc agagtacgcg gggaaaacaa    60
aaacctcaaa ctgaacaaca ttcaatatta gtgaaacact ttttactctc tcaaa         115
```

<210> SEQ ID NO 38
<211> LENGTH: 81
<212> TYPE: DNA
<213> ORGANISM: Petunia x hybrida v26

<400> SEQUENCE: 38

```
gaagaaacaa aaacctcaaa ctgaaataac attcagtact agtactatac acttttaca    60
```
caaaatatca gtgatcaaga a                                              81

<210> SEQ ID NO 39
<211> LENGTH: 90
<212> TYPE: DNA
<213> ORGANISM: Petunia x hybrida v26

<400> SEQUENCE: 39
gaaaataaaa acaaaaacct caaactgaaa taacattcag tactagtact atacacttac   60
tattactctc aaaatatgag tgatcaagaa                                     90

<210> SEQ ID NO 40
<211> LENGTH: 711
<212> TYPE: DNA
<213> ORGANISM: Petunia x hybrida v26

<400> SEQUENCE: 40
atggatatct ttggaagcta ttattcagac acacttcctg cagcatcagc tcctactttt   60
tggcctttag acgtgcctga atattcttca ccaatatctg ataatagcag ctgcagtaat  120
aatagagcta atcattctga tgaagaggtg atgttagctt caaataaccc gaaaaagcga  180
gccgggagga agaagtttag agaaacacga catccagtat acaggggagt caggaagagg  240
aattcaggca agtgggtttg tgaagtgaga gaacccaata agcaatcaag aatttggctt  300
ggaacattcc caactgctga atggcggct agagctcatg acgtggcggc tattgcattt  360
aggggtcgtt ctgcttgttt gaattttgcg gactctgctt ggaagttgcc taccccctgct  420 tcttccgacc ccaaggatat tcagaaggcg gccgcagagg ccgccgaggc ttttaggcct  480
ttggagtcag aaggggtaca ttcagctgga gaagaatcaa agaagagag caccactcca  540 gaaacagcag agagtatgta ctttatggat gaagaggcac tttctctgcat gcctggatta  600 cttgcaaata tggctgaagg gctaatgtta cctccacctc aatgttcaga gttggagat  660 cattttatgg aagctgatgc tgacatgcct ttatggagtt attctgtcta a            711

<210> SEQ ID NO 41
<211> LENGTH: 660
<212> TYPE: DNA
<213> ORGANISM: Petunia v hybrida v26

<400> SEQUENCE: 41
atggatatct ttggaagcta ttattcagac atacttccta tagaattgcc tgaatattct   60
tcaccaatgt ctgacaatag cagctgcagc aattatagag ctaatcattc agatgacgaa  120
gtgatgttag cttcaaataa ccccaagaag tgtgctggga ggaagaagtt tagagaaaca  180
cgacatccag tatacagggg agtcaggaag aggaacggca agtgggtttg tgaagtcaga  240
gagcccaata agaaatcaag aatttggctt ggttcatttc caactgctga atggccgct  300 agagctcacg atgtagcggc tattgcatta aggggtcgtt ctgcttgctt gaactttgct  360
gactctgctt ggaagttgcc tatccctgct tcctccaacc ccaaggatat tcagaaggcg  420
gccgcagagg ccgccaaggc tttcagggag tcggagaag aatcaaagga agagagcagt  480
actcgtgaaa cgccagaaaa gatgttcttt atggatgaag aggcactttt ctgcatgcca  540
gaattacttg caaatatggc tgaaggacta atgttacctc caccatctca atgttcagat  600
gttggagagc attttatgga tgctgatgtt gacatgcctt tatggagtta ttctatctaa  660

<210> SEQ ID NO 42
<211> LENGTH: 669

```
<212> TYPE: DNA
<213> ORGANISM: Petunia x hybrida v26

<400> SEQUENCE: 42
atggatattt tgcaagata ttattcggac caacttccta tagcatcagc tgctactttt    60
tggccttag aagtggctga atattcttca ccaatgtctg atattagtaa taatagagct   120
aatctttcag atgaagaagt gatgttagct tcaaataacc caagaagcg agctgggagg   180
aagaagtttc aagaaacacg acatccagta tacaggggag tgaggaagag gagttcaggc   240
aagtggtttt gtgaagtgag agagcccaat aagaaatcaa gaatttggct aggcacatat   300
ataactgctg aaatggcagc tagagctcat gacgtcgcag ctattgcatt aagggggtcgt  360
tctgcttgtc tgaactttgc tgactctgct tggaagttgc atatcccggc ttcctccaaa   420
gccaaggata ttcagaaggc ggccacagag gctgcctcgg cttttccagga atcaaaggaa   480
gagggcacta ctcctgaaac gccagaaaag atgctcttta tggatgaaga ggcacttttc   540
tacatgcctg gattacttgc aaatatggct gaaggactaa tgttacctct accacctcaa   600
tgttcagaag ttggagatca tttatatgga gctgctgctg acatgcctt gtggagttat   660
tctttctaa                                                           669

<210> SEQ ID NO 43
<211> LENGTH: 648
<212> TYPE: DNA
<213> ORGANISM: Petunia x hybrida v26

<400> SEQUENCE: 43
atggatattt tggacgata ttattctgac caacttccta tagcatcagc tgctacattt    60
tggccttag aagtggctga atattctgat aatagcagca gcagcagtaa taatagagct   120
aatgtttcag atgaagaagt gatgttagct tcaaataacc caagaagcg agctgggagg   180
aagaagtttc aagaaactcg acatccagta tataggggag tgaggaagag gaattcaggg   240
aagtggttt gtgaagtgag agagcccaat aagaaatcaa gaatatggct tggaacatat   300
tcaactgcag aaatggcagc tagagctcat gatgttgcgg ctattgcatt aagggggtcgt  360
gctgcttgtc taaactttgc tgactctgct tggaagttac ctatcccggc ttcctccaaa   420
gccaaggata tccagaaggc ggccacagag gccgccgcca cggcttttct ggaaccagga   480
gagcctgaaa ctcgaaaaaa aaatatgttg tttatggatg aagaggcact tttttgcatg   540
cctggattac ttgcaaatat ggctgaagga ctaatgttaa ctccacctca atgttatgga   600
gaacatttta tggaagctga tgctgaagtg cctttatgga gttattag                648

<210> SEQ ID NO 44
<211> LENGTH: 61
<212> TYPE: PRT
<213> ORGANISM: Petunia x hybrida v26

<400> SEQUENCE: 44

Pro Val Tyr Arg Gly Val Arg Lys Arg Asn Ser Gly Lys Trp Val Cys
1               5                   10                  15

Glu Val Arg Glu Pro Asn Lys Gln Ser Arg Ile Trp Leu Gly Thr Phe
            20                  25                  30

Pro Thr Ala Glu Met Ala Ala Arg Ala His Asp Val Ala Ala Ile Ala
        35                  40                  45

Phe Arg Gly Arg Ser Ala Cys Leu Asn Phe Ala Asp Ser
    50                  55                  60
```

```
<210> SEQ ID NO 45
<211> LENGTH: 60
<212> TYPE: PRT
<213> ORGANISM: Petunia x hybrida v26

<400> SEQUENCE: 45

Pro Val Tyr Arg Gly Val Arg Lys Arg Asn Gly Lys Trp Val Cys Glu
1               5                   10                  15

Val Arg Glu Pro Asn Lys Lys Ser Arg Ile Trp Leu Gly Ser Phe Pro
            20                  25                  30

Thr Ala Glu Met Ala Ala Val Ala His Asp Val Ala Ala Ile Lys Leu
        35                  40                  45

Arg Gly Pro Asp Ala Leu Thr Asn Phe Ala Asp Ser
    50                  55                  60

<210> SEQ ID NO 46
<211> LENGTH: 236
<212> TYPE: PRT
<213> ORGANISM: Petunia x hybrida v26

<400> SEQUENCE: 46

Met Asp Ile Phe Gly Ser Tyr Tyr Ser Asp Thr Leu Pro Ala Ala Ser
1               5                   10                  15

Ala Pro Thr Phe Trp Pro Leu Asp Val Pro Glu Tyr Ser Ser Pro Ile
            20                  25                  30

Ser Asp Asn Ser Ser Cys Ser Asn Arg Ala Asn His Ser Asp Glu
        35                  40                  45

Glu Val Met Leu Ala Ser Asn Asn Pro Lys Lys Arg Ala Gly Arg Lys
    50                  55                  60

Lys Phe Arg Glu Thr Arg His Pro Val Tyr Arg Gly Val Arg Lys Arg
65                  70                  75                  80

Asn Ser Gly Lys Trp Val Cys Glu Val Arg Glu Pro Asn Lys Gln Ser
                85                  90                  95

Arg Ile Trp Leu Gly Thr Phe Pro Thr Ala Glu Met Ala Ala Val Ala
            100                 105                 110

His Asp Val Ala Ala Ile Lys Phe Arg Gly Val Glu Ala Asp Ile Asn
        115                 120                 125

Phe Ala Asp Ser Ala Trp Lys Leu Pro Thr Pro Ala Ser Ser Asp Pro
    130                 135                 140

Lys Asp Ile Gln Lys Ala Ala Ala Glu Ala Glu Ala Phe Arg Pro
145                 150                 155                 160

Leu Glu Ser Glu Gly Val His Ser Ala Gly Glu Ser Lys Glu Glu
                165                 170                 175

Ser Thr Thr Pro Glu Thr Ala Gly Ser Met Tyr Phe Met Asp Glu Glu
            180                 185                 190

Ala Leu Phe Cys Met Pro Gly Leu Leu Ala Asn Met Ala Glu Gly Leu
        195                 200                 205

Met Leu Pro Pro Pro Gln Cys Ser Glu Val Gly Asp His Phe Met Glu
    210                 215                 220

Ala Asp Ala Asp Met Pro Leu Trp Ser Tyr Ser Val
225                 230                 235

<210> SEQ ID NO 47
<211> LENGTH: 236
<212> TYPE: PRT
<213> ORGANISM: Petunia x hybrida v26

<400> SEQUENCE: 47
```

```
Met Asp Ile Phe Gly Ser Tyr Tyr Ser Asp Thr Leu Pro Ala Ala Ser
1               5                   10                  15

Ala Pro Thr Phe Trp Pro Leu Asp Val Pro Glu Tyr Ser Ser Pro Ile
            20                  25                  30

Ser Asp Asn Ser Ser Cys Ser Asn Asn Arg Ala Asn His Ser Asp Glu
        35                  40                  45

Glu Val Met Leu Ala Ser Asn Asn Pro Lys Lys Arg Ala Gly Arg Lys
    50                  55                  60

Lys Phe Arg Glu Thr Arg His Pro Val Tyr Arg Gly Val Arg Lys Arg
65              70                  75                  80

Asn Ser Gly Lys Trp Val Cys Glu Val Arg Glu Pro Asn Lys Gln Ser
            85                  90                  95

Arg Ile Trp Leu Gly Thr Phe Pro Thr Ala Glu Met Ala Ala Val Ala
                100                 105                 110

His Asp Val Ala Ala Ile Lys Phe Arg Gly Thr Asn Ala Val Thr Asn
        115                 120                 125

Phe Ala Asp Ser Ala Trp Lys Leu Pro Thr Pro Ala Ser Ser Asp Pro
130                 135                 140

Lys Asp Ile Gln Lys Ala Ala Glu Ala Ala Glu Ala Phe Arg Pro
145                 150                 155                 160

Leu Glu Ser Glu Gly Val His Ser Ala Gly Glu Ser Lys Glu Glu
                165                 170                 175

Ser Thr Thr Pro Glu Thr Ala Glu Ser Met Tyr Phe Met Asp Glu Glu
            180                 185                 190

Ala Leu Phe Cys Met Pro Gly Leu Leu Ala Asn Met Ala Glu Gly Leu
                195                 200                 205

Met Leu Pro Pro Pro Gln Cys Ser Glu Val Gly Asp His Phe Met Glu
210                 215                 220

Ala Asp Ala Asp Met Pro Leu Trp Ser Tyr Ser Val
225                 230                 235

<210> SEQ ID NO 48
<211> LENGTH: 236
<212> TYPE: PRT
<213> ORGANISM: Petunia x hybrida v26

<400> SEQUENCE: 48

Met Asp Ile Phe Gly Ser Tyr Tyr Ser Asp Thr Leu Pro Ala Ala Ser
1               5                   10                  15

Ala Pro Thr Phe Trp Pro Leu Asp Val Pro Glu Tyr Ser Ser Pro Ile
            20                  25                  30

Ser Asp Asn Ser Ser Cys Ser Asn Asn Arg Ala Asn His Ser Asp Glu
        35                  40                  45

Glu Val Met Leu Ala Ser Asn Asn Pro Lys Lys Arg Ala Gly Arg Lys
    50                  55                  60

Lys Phe Arg Glu Thr Arg His Pro Val Tyr Arg Gly Val Arg Lys Arg
65              70                  75                  80

Asn Ser Gly Lys Trp Val Cys Glu Val Arg Glu Pro Asn Arg Gln Ser
            85                  90                  95

Arg Ile Trp Leu Gly Thr Phe Pro Thr Ala Glu Met Ala Ala Lys Ala
                100                 105                 110

Tyr Asp Ile Ala Ala Val Ala Phe Arg Gly Arg Ser Ala Cys Ile Asn
        115                 120                 125

Phe Ala Asp Ser Ala Trp Lys Leu Pro Thr Pro Ala Ser Ser Asp Pro
130                 135                 140
```

```
Lys Asp Ile Gln Lys Ala Ala Glu Ala Ala Glu Ala Phe Arg Pro
145                 150                 155                 160

Leu Glu Ser Glu Gly Val His Ser Ala Gly Glu Ser Lys Glu Glu
                165                 170                 175

Ser Thr Thr Pro Glu Thr Ala Glu Ser Met Tyr Phe Met Asp Glu Glu
                180                 185                 190

Ala Leu Phe Cys Met Pro Gly Leu Leu Ala Asn Met Ala Glu Gly Leu
            195                 200                 205

Met Leu Pro Pro Pro Gln Cys Ser Glu Val Gly Asp His Phe Met Glu
210                 215                 220

Ala Asp Ala Asp Met Pro Leu Trp Ser Tyr Ser Val
225                 230                 235

<210> SEQ ID NO 49
<211> LENGTH: 219
<212> TYPE: PRT
<213> ORGANISM: Petunia x hybrida v26

<400> SEQUENCE: 49

Met Asp Ile Phe Gly Ser Tyr Tyr Ser Asp Ile Leu Pro Ile Glu Leu
1               5                   10                  15

Pro Glu Tyr Ser Ser Pro Met Ser Asp Asn Ser Ser Cys Ser Asn Tyr
                20                  25                  30

Arg Ala Asn His Ser Asp Asp Glu Val Met Leu Ala Ser Asn Asn Pro
            35                  40                  45

Lys Lys Cys Ala Gly Arg Lys Lys Phe Arg Glu Thr Arg His Pro Val
50                  55                  60

Tyr Arg Gly Val Arg Lys Arg Asn Gly Lys Trp Val Cys Glu Val Arg
65                  70                  75                  80

Glu Pro Asn Lys Lys Ser Arg Ile Trp Leu Gly Ser Phe Pro Thr Ala
                85                  90                  95

Glu Met Ala Ala Val Ala His Asp Val Ala Ala Ile Lys Leu Arg Gly
            100                 105                 110

Pro Asp Ala Leu Thr Asn Phe Ala Asp Ser Ala Trp Lys Leu Pro Ile
        115                 120                 125

Pro Ala Ser Ser Asn Pro Lys Asp Ile Gln Lys Ala Ala Glu Ala
130                 135                 140

Ala Lys Ala Phe Arg Glu Ser Gly Glu Glu Ser Lys Glu Glu Ser Ser
145                 150                 155                 160

Thr Arg Glu Thr Pro Glu Lys Met Phe Phe Met Asp Glu Glu Ala Leu
                165                 170                 175

Phe Cys Met Pro Glu Leu Leu Ala Asn Met Ala Glu Gly Leu Met Leu
            180                 185                 190

Pro Pro Pro Ser Gln Cys Ser Asp Val Gly Glu His Phe Met Asp Ala
        195                 200                 205

Asp Val Asp Met Pro Leu Trp Ser Tyr Ser Ile
    210                 215

<210> SEQ ID NO 50
<211> LENGTH: 219
<212> TYPE: PRT
<213> ORGANISM: Petunia x hybrida v26

<400> SEQUENCE: 50

Met Asp Ile Phe Gly Ser Tyr Tyr Ser Asp Ile Leu Pro Ile Glu Leu
1               5                   10                  15

Pro Glu Tyr Ser Ser Pro Met Ser Asp Asn Ser Ser Cys Ser Asn Tyr
```

```
            20                  25                  30
Arg Ala Asn His Ser Asp Asp Glu Val Met Leu Ala Ser Asn Asn Pro
        35                  40                  45
Lys Lys Cys Ala Gly Arg Lys Lys Phe Arg Glu Thr Arg His Pro Val
    50                  55                  60
Tyr Arg Gly Val Arg Lys Arg Asn Gly Lys Trp Val Cys Glu Val Arg
 65                  70                  75                  80
Glu Pro Asn Lys Lys Ser Arg Ile Trp Leu Gly Ser Phe Pro Thr Ala
                85                  90                  95
Glu Met Ala Ala Leu Ala His Asp Val Ala Ala Ile Lys Leu Arg Gly
            100                 105                 110
Pro Asp Ala Leu Thr Asn Phe Ala Asp Ser Ala Trp Lys Leu Pro Ile
        115                 120                 125
Pro Ala Ser Ser Asn Pro Lys Asp Ile Gln Lys Ala Ala Glu Ala
    130                 135                 140
Ala Lys Ala Phe Arg Glu Ser Gly Glu Glu Ser Lys Glu Glu Ser Ser
145                 150                 155                 160
Thr Arg Glu Thr Pro Glu Lys Met Phe Phe Met Asp Glu Glu Ala Leu
                165                 170                 175
Phe Cys Met Pro Glu Leu Leu Ala Asn Met Ala Glu Gly Leu Met Leu
            180                 185                 190
Pro Pro Pro Ser Gln Cys Ser Asp Val Gly Glu His Phe Met Asp Ala
        195                 200                 205
Asp Val Asp Met Pro Leu Trp Ser Tyr Ser Ile
    210                 215

<210> SEQ ID NO 51
<211> LENGTH: 219
<212> TYPE: PRT
<213> ORGANISM: Petunia x hybrida v26

<400> SEQUENCE: 51

Met Asp Ile Phe Gly Ser Tyr Tyr Ser Asp Ile Leu Pro Ile Glu Leu
 1                   5                  10                  15
Pro Glu Tyr Ser Ser Pro Met Ser Asp Asn Ser Ser Cys Ser Asn Tyr
                20                  25                  30
Arg Ala Asn His Ser Asp Asp Glu Val Met Leu Ala Ser Asn Asn Pro
        35                  40                  45
Lys Lys Cys Ala Gly Arg Lys Lys Phe Arg Glu Thr Arg His Pro Val
    50                  55                  60
Tyr Arg Gly Val Arg Lys Arg Asn Gly Lys Trp Val Cys Glu Val Arg
 65                  70                  75                  80
Glu Pro Asn Arg Lys Ser Arg Ile Trp Leu Gly Ser Phe Pro Thr Ala
                85                  90                  95
Glu Met Ala Ala Lys Ala Tyr Asp Ile Ala Ala Val Ala Leu Arg Gly
            100                 105                 110
Arg Ser Ala Cys Ile Asn Phe Ala Asp Ser Ala Trp Lys Leu Pro Ile
        115                 120                 125
Pro Ala Ser Ser Asn Pro Lys Asp Ile Gln Lys Ala Ala Ala Glu Ala
    130                 135                 140
Ala Lys Ala Phe Arg Glu Ser Gly Glu Glu Ser Lys Glu Glu Ser Ser
145                 150                 155                 160
Thr Arg Glu Thr Pro Glu Lys Met Phe Phe Met Asp Glu Glu Ala Leu
                165                 170                 175
Phe Cys Met Pro Glu Leu Leu Ala Asn Met Ala Glu Gly Leu Met Leu
```

```
                    180                 185                 190
Pro Pro Pro Ser Gln Cys Ser Asp Val Gly Glu His Phe Met Asp Ala
            195                 200                 205

Asp Val Asp Met Pro Leu Trp Ser Tyr Ser Ile
            210                 215

<210> SEQ ID NO 52
<211> LENGTH: 222
<212> TYPE: PRT
<213> ORGANISM: Petunia x hybrida v26

<400> SEQUENCE: 52

Met Asp Ile Phe Ala Arg Tyr Tyr Ser Asp Gln Leu Pro Ile Ala Ser
1               5                   10                  15

Ala Ala Thr Phe Trp Pro Leu Glu Val Ala Glu Tyr Ser Ser Pro Met
            20                  25                  30

Ser Asp Ile Ser Asn Asn Arg Ala Asn Leu Ser Asp Glu Glu Val Met
        35                  40                  45

Leu Ala Ser Asn Asn Pro Lys Lys Arg Ala Gly Arg Lys Lys Phe Gln
    50                  55                  60

Glu Thr Arg His Pro Val Tyr Arg Gly Val Arg Lys Arg Ser Ser Gly
65                  70                  75                  80

Lys Trp Val Cys Glu Val Arg Glu Pro Asn Lys Lys Ser Arg Ile Trp
                85                  90                  95

Leu Gly Thr Tyr Ile Thr Ala Glu Met Ala Ala Leu Ala His Asp Val
            100                 105                 110

Ala Ala Ile Lys Leu Arg Gly Pro Asp Ala Leu Thr Asn Phe Ala Asp
        115                 120                 125

Ser Ala Trp Lys Leu His Ile Pro Ala Ser Ser Lys Ala Lys Asp Ile
    130                 135                 140

Gln Lys Ala Ala Thr Glu Ala Ala Ser Ala Phe Gln Glu Ser Lys Glu
145                 150                 155                 160

Glu Gly Thr Thr Pro Glu Thr Pro Glu Lys Met Leu Phe Met Asp Glu
                165                 170                 175

Glu Ala Leu Phe Tyr Met Pro Gly Leu Leu Ala Asn Met Ala Glu Gly
            180                 185                 190

Leu Met Leu Pro Leu Pro Pro Gln Cys Ser Glu Val Gly Asp His Phe
        195                 200                 205

Met Glu Ala Ala Ala Asp Met Pro Leu Trp Ser Tyr Ser Phe
    210                 215                 220

<210> SEQ ID NO 53
<211> LENGTH: 222
<212> TYPE: PRT
<213> ORGANISM: Petunia x hybrida v26

<400> SEQUENCE: 53

Met Asp Ile Phe Ala Arg Tyr Tyr Ser Asp Gln Leu Pro Ile Ala Ser
1               5                   10                  15

Ala Ala Thr Phe Trp Pro Leu Glu Val Ala Glu Tyr Ser Ser Pro Met
            20                  25                  30

Ser Asp Ile Ser Asn Asn Arg Ala Asn Leu Ser Asp Glu Glu Val Met
        35                  40                  45

Leu Ala Ser Asn Asn Pro Lys Lys Arg Ala Gly Arg Lys Lys Phe Gln
    50                  55                  60

Glu Thr Arg His Pro Val Tyr Arg Gly Val Arg Lys Arg Ser Ser Gly
65                  70                  75                  80
```

```
Lys Trp Val Cys Glu Val Arg Glu Pro Asn Lys Lys Ser Arg Ile Trp
                85                  90                  95
Leu Gly Thr Tyr Ile Thr Ala Glu Met Ala Ala Val Ala His Asp Val
            100                 105                 110
Ala Ala Ile Lys Leu Arg Gly Pro Asp Ala Leu Thr Asn Phe Ala Asp
        115                 120                 125
Ser Ala Trp Lys Leu His Ile Pro Ala Ser Ser Lys Ala Lys Asp Ile
    130                 135                 140
Gln Lys Ala Ala Thr Glu Ala Ala Ser Ala Phe Gln Glu Ser Lys Glu
145                 150                 155                 160
Glu Gly Thr Thr Pro Glu Thr Pro Glu Lys Met Leu Phe Met Asp Glu
                165                 170                 175
Glu Ala Leu Phe Tyr Met Pro Gly Leu Leu Ala Asn Met Ala Glu Gly
            180                 185                 190
Leu Met Leu Pro Leu Pro Pro Gln Cys Ser Glu Val Gly Asp His Phe
        195                 200                 205
Met Glu Ala Ala Ala Asp Met Pro Leu Trp Ser Tyr Ser Phe
    210                 215                 220
```

<210> SEQ ID NO 54
<211> LENGTH: 222
<212> TYPE: PRT
<213> ORGANISM: Petunia x hybrida v26

<400> SEQUENCE: 54

```
Met Asp Ile Phe Ala Arg Tyr Tyr Ser Asp Gln Leu Pro Ile Ala Ser
1               5                   10                  15
Ala Ala Thr Phe Trp Pro Leu Glu Val Ala Glu Tyr Ser Ser Pro Met
            20                  25                  30
Ser Asp Ile Ser Asn Asn Arg Ala Asn Leu Ser Asp Glu Glu Val Met
        35                  40                  45
Leu Ala Ser Asn Asn Pro Lys Lys Arg Ala Gly Arg Lys Lys Phe Gln
    50                  55                  60
Glu Thr Arg His Pro Val Tyr Arg Gly Val Arg Lys Arg Ser Ser Gly
65                  70                  75                  80
Lys Trp Val Cys Glu Val Arg Glu Pro Asn Arg Lys Ser Arg Ile Trp
                85                  90                  95
Leu Gly Thr Tyr Ile Thr Ala Glu Met Ala Ala Lys Ala His Asp Ile
            100                 105                 110
Ala Ala Val Ala Leu Arg Gly Arg Ser Ala Cys Ile Asn Phe Ala Asp
        115                 120                 125
Ser Ala Trp Lys Leu His Ile Pro Ala Ser Ser Lys Ala Lys Asp Ile
    130                 135                 140
Gln Lys Ala Ala Thr Glu Ala Ala Ser Ala Phe Gln Glu Ser Lys Glu
145                 150                 155                 160
Glu Gly Thr Thr Pro Glu Thr Pro Glu Lys Met Leu Phe Met Asp Glu
                165                 170                 175
Glu Ala Leu Phe Tyr Met Pro Gly Leu Leu Ala Asn Met Ala Glu Gly
            180                 185                 190
Leu Met Leu Pro Leu Pro Pro Gln Cys Ser Glu Val Gly Asp His Phe
        195                 200                 205
Met Glu Ala Ala Ala Asp Met Pro Leu Trp Ser Tyr Ser Phe
    210                 215                 220
```

<210> SEQ ID NO 55

```
<211> LENGTH: 222
<212> TYPE: PRT
<213> ORGANISM: Petunia x hybrida v26

<400> SEQUENCE: 55

Met Asp Ile Phe Ala Arg Tyr Tyr Ser Asp Gln Leu Pro Ile Ala Ser
1               5                   10                  15

Ala Ala Thr Phe Trp Pro Leu Glu Val Ala Glu Tyr Ser Ser Pro Met
            20                  25                  30

Ser Asp Ile Ser Asn Asn Arg Ala Asn Leu Ser Asp Glu Glu Val Met
        35                  40                  45

Leu Ala Ser Asn Asn Pro Lys Lys Arg Ala Gly Arg Lys Lys Phe Gln
    50                  55                  60

Glu Thr Arg His Pro Val Tyr Arg Gly Val Arg Lys Arg Ser Ser Gly
65                  70                  75                  80

Lys Trp Val Cys Glu Val Arg Glu Pro Asn Lys Lys Ser Arg Ile Trp
                85                  90                  95

Leu Gly Thr Tyr Ile Thr Ala Glu Met Ala Ala Lys Ala Tyr Asp Ile
            100                 105                 110

Ala Ala Val Ala Leu Arg Gly Arg Ser Ala Cys Ile Asn Phe Ala Asp
        115                 120                 125

Ser Ala Trp Lys Leu His Ile Pro Ala Ser Ser Lys Ala Lys Asp Ile
    130                 135                 140

Gln Lys Ala Ala Thr Glu Ala Ala Ser Ala Phe Gln Glu Ser Lys Glu
145                 150                 155                 160

Glu Gly Thr Thr Pro Glu Thr Pro Glu Lys Met Leu Phe Met Asp Glu
                165                 170                 175

Glu Ala Leu Phe Tyr Met Pro Gly Leu Leu Ala Asn Met Ala Glu Gly
            180                 185                 190

Leu Met Leu Pro Leu Pro Pro Gln Cys Ser Glu Val Gly Asp His Phe
        195                 200                 205

Met Glu Ala Ala Ala Asp Met Pro Leu Trp Ser Tyr Ser Phe
    210                 215                 220

<210> SEQ ID NO 56
<211> LENGTH: 215
<212> TYPE: PRT
<213> ORGANISM: Petunia x hybrida v26

<400> SEQUENCE: 56

Met Asp Ile Phe Gly Arg Tyr Tyr Ser Asp Gln Leu Pro Ile Ala Ser
1               5                   10                  15

Ala Ala Thr Phe Trp Pro Leu Glu Val Ala Glu Tyr Ser Asp Asn Ser
            20                  25                  30

Ser Ser Ser Ser Asn Asn Arg Ala Asn Val Ser Asp Glu Glu Val Met
        35                  40                  45

Leu Ala Ser Asn Asn Pro Lys Lys Arg Ala Gly Arg Lys Lys Phe Gln
    50                  55                  60

Glu Thr Arg His Pro Val Tyr Arg Gly Val Arg Lys Arg Asn Ser Gly
65                  70                  75                  80

Lys Trp Val Cys Glu Val Arg Glu Pro Asn Lys Lys Ser Arg Ile Trp
                85                  90                  95

Leu Gly Thr Tyr Ser Thr Ala Glu Met Ala Ala Leu Ala His Asp Arg
            100                 105                 110

Ala Ala Ile Lys Leu Arg Gly Pro Asp Ala Leu Thr Asn Phe Ala Asp
        115                 120                 125
```

```
Ser Ala Trp Lys Leu Pro Ile Pro Ala Ser Ser Lys Ala Lys Asp Ile
        130                 135                 140

Gln Lys Ala Ala Thr Glu Ala Ala Thr Ala Phe Leu Glu Pro Gly
145                 150                 155                 160

Glu Pro Glu Thr Arg Lys Lys Asn Met Leu Phe Met Asp Glu Ala
                165                 170                 175

Leu Phe Cys Met Pro Gly Leu Leu Ala Asn Met Ala Glu Gly Leu Met
            180                 185                 190

Leu Thr Pro Pro Gln Cys Tyr Gly Glu His Phe Met Glu Ala Asp Ala
        195                 200                 205

Glu Val Pro Leu Trp Ser Tyr
    210                 215

<210> SEQ ID NO 57
<211> LENGTH: 215
<212> TYPE: PRT
<213> ORGANISM: Petunia x hybrida v26

<400> SEQUENCE: 57

Met Asp Ile Phe Gly Arg Tyr Tyr Ser Asp Gln Leu Pro Ile Ala Ser
1               5                   10                  15

Ala Ala Thr Phe Trp Pro Leu Glu Val Ala Glu Tyr Ser Asp Asn Ser
            20                  25                  30

Ser Ser Ser Asn Asn Arg Ala Asn Val Ser Asp Glu Val Met
        35                  40                  45

Leu Ala Ser Asn Asn Pro Lys Lys Arg Ala Gly Arg Lys Lys Phe Gln
50                  55                  60

Glu Thr Arg His Pro Val Tyr Arg Gly Val Arg Lys Arg Asn Ser Gly
65                  70                  75                  80

Lys Trp Val Cys Glu Val Arg Glu Pro Asn Lys Lys Ser Arg Ile Trp
                85                  90                  95

Leu Gly Thr Tyr Ser Thr Ala Glu Met Ala Ala Val Ala His Asp Arg
            100                 105                 110

Ala Ala Ile Lys Leu Arg Gly Pro Asp Ala Leu Thr Asn Phe Ala Asp
        115                 120                 125

Ser Ala Trp Lys Leu Pro Ile Pro Ala Ser Ser Lys Ala Lys Asp Ile
130                 135                 140

Gln Lys Ala Ala Thr Glu Ala Ala Thr Ala Phe Leu Glu Pro Gly
145                 150                 155                 160

Glu Pro Glu Thr Arg Lys Lys Asn Met Leu Phe Met Asp Glu Ala
                165                 170                 175

Leu Phe Cys Met Pro Gly Leu Leu Ala Asn Met Ala Glu Gly Leu Met
            180                 185                 190

Leu Thr Pro Pro Gln Cys Tyr Gly Glu His Phe Met Glu Ala Asp Ala
        195                 200                 205

Glu Val Pro Leu Trp Ser Tyr
    210                 215

<210> SEQ ID NO 58
<211> LENGTH: 215
<212> TYPE: PRT
<213> ORGANISM: Petunia x hybrida v26

<400> SEQUENCE: 58

Met Asp Ile Phe Gly Arg Tyr Tyr Ser Asp Gln Leu Pro Ile Ala Ser
1               5                   10                  15

Ala Ala Thr Phe Trp Pro Leu Glu Val Ala Glu Tyr Ser Asp Asn Ser
```

```
            20                  25                  30
Ser Ser Ser Ser Asn Asn Arg Ala Asn Val Ser Asp Glu Glu Val Met
        35                  40                  45
Leu Ala Ser Asn Asn Pro Lys Lys Arg Ala Gly Arg Lys Lys Phe Gln
    50                  55                  60
Glu Thr Arg His Pro Val Tyr Arg Gly Val Arg Lys Arg Asn Ser Gly
65                  70                  75                  80
Lys Trp Val Cys Glu Val Arg Glu Pro Asn Lys Lys Ser Arg Ile Trp
                85                  90                  95
Leu Gly Thr Tyr Ser Thr Ala Glu Met Ala Ala Leu Ala His Asp Ile
            100                 105                 110
Ala Ala Ile Lys Leu Arg Gly Pro Asp Ala Leu Thr Asn Phe Ala Asp
        115                 120                 125
Ser Ala Trp Lys Leu Pro Ile Pro Ala Ser Ser Lys Ala Lys Asp Ile
    130                 135                 140
Gln Lys Ala Ala Thr Glu Ala Ala Ala Thr Ala Phe Leu Glu Pro Gly
145                 150                 155                 160
Glu Pro Glu Thr Arg Lys Lys Asn Met Leu Phe Met Asp Glu Ala
                165                 170                 175
Leu Phe Cys Met Pro Gly Leu Leu Ala Asn Met Ala Glu Gly Leu Met
            180                 185                 190
Leu Thr Pro Pro Gln Cys Tyr Gly Glu His Phe Met Glu Ala Asp Ala
        195                 200                 205
Glu Val Pro Leu Trp Ser Tyr
    210                 215

<210> SEQ ID NO 59
<211> LENGTH: 215
<212> TYPE: PRT
<213> ORGANISM: Petunia x hybrida v26

<400> SEQUENCE: 59

Met Asp Ile Phe Gly Arg Tyr Tyr Ser Asp Gln Leu Pro Ile Ala Ser
1               5                   10                  15
Ala Ala Thr Phe Trp Pro Leu Glu Val Ala Glu Tyr Ser Asp Asn Ser
            20                  25                  30
Ser Ser Ser Ser Asn Asn Arg Ala Asn Val Ser Asp Glu Glu Val Met
        35                  40                  45
Leu Ala Ser Asn Asn Pro Lys Lys Arg Ala Gly Arg Lys Lys Phe Gln
    50                  55                  60
Glu Thr Arg His Pro Val Tyr Arg Gly Val Arg Lys Arg Asn Ser Gly
65                  70                  75                  80
Lys Trp Val Cys Glu Val Arg Glu Pro Asn Lys Lys Ser Arg Ile Trp
                85                  90                  95
Leu Gly Thr Tyr Ser Thr Ala Glu Met Ala Ala Val Ala His Asp Ile
            100                 105                 110
Ala Ala Ile Lys Leu Arg Gly Pro Asp Ala Leu Thr Asn Phe Ala Asp
        115                 120                 125
Ser Ala Trp Lys Leu Pro Ile Pro Ala Ser Ser Lys Ala Lys Asp Ile
    130                 135                 140
Gln Lys Ala Ala Thr Glu Ala Ala Ala Thr Ala Phe Leu Glu Pro Gly
145                 150                 155                 160
Glu Pro Glu Thr Arg Lys Lys Asn Met Leu Phe Met Asp Glu Ala
                165                 170                 175
Leu Phe Cys Met Pro Gly Leu Leu Ala Asn Met Ala Glu Gly Leu Met
```

```
                        180                 185                 190
Leu Thr Pro Pro Gln Cys Tyr Gly Glu His Phe Met Glu Ala Asp Ala
            195                 200                 205

Glu Val Pro Leu Trp Ser Tyr
        210                 215

<210> SEQ ID NO 60
<211> LENGTH: 215
<212> TYPE: PRT
<213> ORGANISM: Petunia x hybrida v26

<400> SEQUENCE: 60

Met Asp Ile Phe Gly Arg Tyr Tyr Ser Asp Gln Leu Pro Ile Ala Ser
1               5                   10                  15

Ala Ala Thr Phe Trp Pro Leu Glu Val Ala Glu Tyr Ser Asp Asn Ser
            20                  25                  30

Ser Ser Ser Ser Asn Asn Arg Ala Asn Val Ser Asp Glu Glu Val Met
        35                  40                  45

Leu Ala Ser Asn Asn Pro Lys Lys Arg Ala Gly Arg Lys Lys Phe Gln
    50                  55                  60

Glu Thr Arg His Pro Val Tyr Arg Gly Val Arg Lys Arg Asn Ser Gly
65                  70                  75                  80

Lys Trp Val Cys Glu Val Arg Glu Pro Asn Arg Lys Ser Arg Ile Trp
                85                  90                  95

Leu Gly Thr Tyr Ser Thr Ala Glu Met Ala Ala Lys Ala His Asp Ile
            100                 105                 110

Ala Ala Val Ala Leu Arg Gly Arg Ala Ala Cys Ile Asn Phe Ala Asp
        115                 120                 125

Ser Ala Trp Lys Leu Pro Ile Pro Ala Ser Ser Lys Ala Lys Asp Ile
    130                 135                 140

Gln Lys Ala Ala Thr Glu Ala Ala Thr Ala Phe Leu Glu Pro Gly
145                 150                 155                 160

Glu Pro Glu Thr Arg Lys Lys Asn Met Leu Phe Met Asp Glu Ala
                165                 170                 175

Leu Phe Cys Met Pro Gly Leu Leu Ala Asn Met Ala Glu Gly Leu Met
            180                 185                 190

Leu Thr Pro Pro Gln Cys Tyr Gly Glu His Phe Met Glu Ala Asp Ala
        195                 200                 205

Glu Val Pro Leu Trp Ser Tyr
    210                 215

<210> SEQ ID NO 61
<211> LENGTH: 215
<212> TYPE: PRT
<213> ORGANISM: Petunia x hybrida v26

<400> SEQUENCE: 61

Met Asp Ile Phe Gly Arg Tyr Tyr Ser Asp Gln Leu Pro Ile Ala Ser
1               5                   10                  15

Ala Ala Thr Phe Trp Pro Leu Glu Val Ala Glu Tyr Ser Asp Asn Ser
            20                  25                  30

Ser Ser Ser Ser Asn Asn Arg Ala Asn Val Ser Asp Glu Glu Val Met
        35                  40                  45

Leu Ala Ser Asn Asn Pro Lys Lys Arg Ala Gly Arg Lys Lys Phe Gln
    50                  55                  60

Glu Thr Arg His Pro Val Tyr Arg Gly Val Arg Lys Arg Asn Ser Gly
65                  70                  75                  80
```

```
Lys Trp Val Cys Glu Val Arg Glu Pro Asn Lys Lys Ser Arg Ile Trp
                 85                  90                  95

Leu Gly Thr Tyr Ser Thr Ala Glu Met Ala Ala Lys Ala Tyr Asp Ile
            100             105                 110

Ala Ala Val Ala Leu Arg Gly Arg Ala Ala Cys Ile Asn Phe Ala Asp
        115             120             125

Ser Ala Trp Lys Leu Pro Ile Pro Ala Ser Ser Lys Ala Lys Asp Ile
    130             135             140

Gln Lys Ala Ala Thr Glu Ala Ala Ala Thr Ala Phe Leu Glu Pro Gly
145             150             155             160

Glu Pro Glu Thr Arg Lys Lys Asn Met Leu Phe Met Asp Glu Glu Ala
            165             170             175

Leu Phe Cys Met Pro Gly Leu Leu Ala Asn Met Ala Glu Gly Leu Met
            180             185             190

Leu Thr Pro Pro Gln Cys Tyr Gly Glu His Phe Met Glu Ala Asp Ala
        195             200             205

Glu Val Pro Leu Trp Ser Tyr
210             215
```